US011208479B2

(12) United States Patent
Jiang et al.

(10) Patent No.: US 11,208,479 B2
(45) Date of Patent: *Dec. 28, 2021

(54) CX43 HEMICHANNEL ANTIBODIES AND METHODS OF USE

(71) Applicant: Board of Regents of the University of Texas System, Austin, TX (US)

(72) Inventors: Jean X. Jiang, Helotes, TX (US); Manuel A. Riquelme, San Antonio, TX (US); Sumin Gu, San Antonio, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/823,762

(22) Filed: Mar. 19, 2020

(65) Prior Publication Data
US 2020/0231669 A1 Jul. 23, 2020

Related U.S. Application Data

(63) Continuation of application No. 15/891,802, filed on Feb. 8, 2018, now Pat. No. 10,633,442, which is a continuation of application No. 14/912,986, filed as application No. PCT/US2014/052206 on Aug. 21, 2014, now Pat. No. 9,914,775.

(60) Provisional application No. 61/868,112, filed on Aug. 21, 2013.

(51) Int. Cl.
*C07K 16/28* (2006.01)
*A61K 49/00* (2006.01)
*G01N 33/50* (2006.01)

(52) U.S. Cl.
CPC .......... *C07K 16/28* (2013.01); *A61K 49/0008* (2013.01); *G01N 33/5032* (2013.01); *C07K 2317/76* (2013.01)

(58) Field of Classification Search
CPC ................ C07K 16/28; C07K 2317/76; A61K 49/0008; G01N 33/5032
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,196,265 A | 4/1980 | Koprowski et al. |
| 4,275,149 A | 6/1981 | Litman et al. |
| 4,277,437 A | 7/1981 | Maggio |
| 4,366,241 A | 12/1982 | Tom et al. |
| 4,469,797 A | 9/1984 | Albarella |
| 4,472,509 A | 9/1984 | Gansow et al. |
| 4,606,855 A | 8/1986 | Deutsch et al. |
| 4,703,003 A | 10/1987 | Struck |
| 4,742,159 A | 5/1988 | Batz et al. |
| 4,767,720 A | 8/1988 | Lingwood |
| 4,816,567 A | 3/1989 | Cabilly et al. |
| 4,867,973 A | 9/1989 | Goers et al. |
| 4,870,287 A | 9/1989 | Cole et al. |
| 4,938,948 A | 7/1990 | Ring et al. |
| 4,946,778 A | 8/1990 | Ladner et al. |
| 5,021,236 A | 6/1991 | Gries et al. |
| 5,091,513 A | 2/1992 | Huston et al. |
| 5,164,296 A | 11/1992 | Blaustein et al. |
| 5,196,066 A | 3/1993 | Kusuda et al. |
| 5,223,409 A | 6/1993 | Ladner et al. |
| 5,403,484 A | 4/1995 | Ladner et al. |
| 5,420,253 A | 5/1995 | Emery et al. |
| 5,565,332 A | 10/1996 | Hoogenboom et al. |
| 5,571,698 A | 11/1996 | Ladner et al. |
| 5,627,052 A | 5/1997 | Schrader |
| 5,656,434 A | 8/1997 | Terano et al. |
| 5,739,169 A | 4/1998 | Ocain et al. |
| 5,760,395 A | 6/1998 | Johnstone |
| 5,770,376 A | 6/1998 | Bagrov |
| 5,789,208 A | 8/1998 | Sharon |
| 5,801,005 A | 9/1998 | Cheever et al. |
| 5,821,337 A | 10/1998 | Carter et al. |
| 5,824,311 A | 10/1998 | Greene et al. |
| 5,830,880 A | 11/1998 | Sedlacek et al. |
| 5,844,091 A | 12/1998 | Blaustein et al. |
| 5,846,945 A | 12/1998 | McCormick |
| 5,858,657 A | 1/1999 | Winter et al. |
| 5,861,155 A | 1/1999 | Lin |
| 5,871,907 A | 2/1999 | Winter et al. |
| 5,969,108 A | 10/1999 | McCafferty et al. |
| 6,054,297 A | 4/2000 | Carter et al. |
| 6,165,464 A | 12/2000 | Hudziak et al. |
| 6,365,157 B2 | 4/2002 | Rockwell et al. |

(Continued)

FOREIGN PATENT DOCUMENTS

CN 1638790 A 7/2005
EP 2700652 A1 2/2014

(Continued)

OTHER PUBLICATIONS

Niger et al. "Interleukin-1β Increases Gap Junctional Communication among Synovial Fibroblasts via the Extracellular Signal Regulated Kinase Pathway", Biol Cell, 102/1, pp. 37-49,Oct. 12, 2009 (Oct. 12, 2009).
Office Action dated Aug. 14, 2020 by the SIPO for CN Application No. 2,921,652, filed on Aug. 21, 2014 (Applicant—Board of Regents of the University of Texas System) (9 Pages).
Office Action dated Jul. 16, 2020 by the CIPO for CA Application No. 201480056187.5, filed on Aug. 21, 2014 (Applicant—Board of Regents of the University ofTexas System) (8 Pages).
Baklaushev et al., Treatment of glioma by cisplatin-loaded nanogels conjugated with monoclonal antibodies against Cx43 and BSAT1. Drug Deliv. 2015; 22(3):276-B5.
Calias et al., Intrathecal delivery of protein therapeutics to the brain: A critical assessment. Pharmacol Thera. 2014; 144:114-22.

(Continued)

Primary Examiner — Robert S Landsman
(74) Attorney, Agent, or Firm — Ballard Spahr LLP

(57) ABSTRACT

Methods for identifying compounds that positively regulate connexin 43 hemichannels.

21 Claims, 17 Drawing Sheets

Specification includes a Sequence Listing.

(56) References Cited

U.S. PATENT DOCUMENTS

| | | |
|---|---|---|
| 6,406,867 B1 | 6/2002 | Yu et al. |
| 6,492,425 B1 | 12/2002 | Callahan et al. |
| 6,709,659 B1 | 3/2004 | Lok et al. |
| 6,709,873 B1 | 3/2004 | Yatscoff et al. |
| 6,753,407 B2 | 6/2004 | Noga et al. |
| 6,814,965 B2 | 11/2004 | Gao et al. |
| 6,849,259 B2 | 2/2005 | Haurum et al. |
| 6,861,572 B1 | 3/2005 | Etches et al. |
| 6,875,434 B1 | 4/2005 | Schenk |
| 6,881,557 B2 | 4/2005 | Foote |
| 6,891,024 B2 | 5/2005 | Marsh |
| 6,946,546 B2 | 9/2005 | Vaughan et al. |
| 7,153,822 B2 | 12/2006 | Jensen et al. |
| 2002/0172677 A1 | 11/2002 | Lahn et al. |
| 2004/0092429 A1 | 5/2004 | Jensen et al. |
| 2004/0126828 A1 | 7/2004 | Karumanchi et al. |
| 2005/0214860 A1 | 9/2005 | Zhu et al. |
| 2007/0042964 A1 | 2/2007 | Jensen et al. |
| 2009/0142295 A1 | 6/2009 | Becker |
| 2011/0243964 A1 | 10/2011 | Duft |
| 2014/0371297 A1 | 12/2014 | Laux et al. |

FOREIGN PATENT DOCUMENTS

| | | |
|---|---|---|
| RU | 2408728 | 1/2011 |
| RU | 2457862 | 8/2012 |
| WO | WO-2003/063891 | 8/2003 |
| WO | WO-2005/116236 | 12/2005 |
| WO | WO-2006/134494 A2 | 12/2006 |
| WO | WO-2013/163423 A1 | 10/2013 |
| WO | WO-2015/027120 A1 | 2/2015 |
| WO | WO-2017/147561 A1 | 8/2017 |

OTHER PUBLICATIONS

Chanson et al., Gap junctional communication in tissue inflammation and repair. Biochim Biophys Acta. 2005; 1711:197-207.

Cochrane et al., Monoclonal antibodies against the connexin43-interacting protein CIP85. Hybridoma (Larchmt). 2009; 28(5):355-61.

Cronin et al., Blocking connexin43 expression reduces inflammation and improves functional recovery after spinal cord injury. Mol Cell Neurosci. 2008; 39(2):152-60.

Huang et al., Critical role of connexin 43 in secondary expansion of traumatic spinal cord injury. J Neurosci. 2012; 32(10):3333-8.

Kielian, Glial connexins and gap junctions in CNS inflammation and disease. J Neurochem. 2008; 106(3):1000-16.

Kolstelny et al., Formation of a Bispecific Antibody by the Use of Leucine Zippers. J Immunol. 1992; 148(5) :1547-53.

Labome, Cx43 Antibody. Cx43 Antibody I Antibody Review Based on Formal Publications. Labome, 2017. Retrieved from Internet: https://www.labome.com/review/gene/human!Cx43-antibody.html, Accessed Jun. 14, 2017.

Lamiche, Influence of connexin 43 on prostatic cancer cells phenotype and on bone metastases development. Universite de Poitiers. Dissertation, pp. 142-189 (2011). Retrieved from Internet: <http://www.opengrey.eu/item/display/10068/887237> on Dec. 5, 2014. (English abstract of French publication).

Li YY, Zhang B, Han F, Liu ZY and Jin FG. Progress on Connexin43. Progress in Modern Biomedicine 2012,12: 3731-3733.

Ilversaro, J. et al., Connexin-mimetic Peptide Gap 27 Decreases Osteoclastic Activity. BMC Musculoskelet Disord. 2001; 2:10.

Maknojia et al., Cx43 function blocking antibody improves outcome and reduces secondary expansion in traumatic spinal cord injury (SCI). AANS, Abstract, Article ID: AA-35194, May 1, 2016.

Nagy et al., Selective monoclonal antibody recognition and cellular localization of an unphosphorylated form of connexin43. Exp Cell Res. 1997; 236(1):127-36.

Niger et al., Interleukin-1 β increases gap junctional communication among synovial fibroblasts via the extracellular-signal-regulated kinase pathway. Biol Cell. 2009; 102(1):37-49.

Orellana et al., Amyloid ~-induced death in neurons involves glial and neuronal hemichannels. J Neurosci. 2011; 31(13):4962-77.

Oviedo-Orta and Evans, Gap junctions and connexin-mediated communication in the immune system. Biochim Biophys Acta. 2004; 1662:102-12.

Perez-Armendariz, E.M. et al., Connexin43 is Expressed in Mouse Fetal Ovary. Anat Rec A. 2003; 271A:360-7.

Plotkin, L.I., Connexin 43 Hemichannels and Intracellular Signaling in Bone Cells. Front Physiol. 2014; 5:131 (8 pages).

Ren et al., Occludin and connexin 43 expression contribute to the pathogenesis of traumatic brain edema. Neural Regen Res. 2013; 8(29):2703-12.

Riquelme et al., Antibodies targeting extracellular domain of connexins for studies of hemichannels. Neuropharmacology. 2013; 75:525-32.

Riquelme, M.A. et al., The ATP Required for Potentiation of Skelatal Muscle Contraction is Released via Pannexin Hemichannels. Neuropharmacology. 2013; 75:594-603.

Siller-Jackson et al., Adaptation of connexin 43-hemichannel prostaglandin release to mechanical loading. J Biol Chem. 2008; 283:26374-82.

Songsivilai, S. and Lachmann, P.J., Bispecific Antibody: a Tool for Diagnosis and Treatment of Disease. Clin Exp Immunol. 1990; 79:315-21.

Ward, E.S. et al., Binding Activities of a Repertoire of Single Immunoglobulin Variable Domains Secreted from *Escherichia coli*. Nature. 1989; 341 (6242):544-6.

Wong et al., the role of gap junctions in inflammatory and neoplastic disorders (Review). Intl J Mol Med. 2017; 39:498-506.

Yusubalieva et al., Antitumor effects of monoclonal antibodies to connexin 43 extracellular fragment in induced low-differentiated glioma. Cell Technol Biol Med. 2012; 1:163-9.

Zhou et al., Osteocytic connexin hemichannels suppress breast cancer growth and bone metastasis. Oncogene. 2016; 35(43):5597-607.

European Search Report and Written Opinion were dated Aug. 28, 2019 by the European Patent Office for EP Application No. 17757405.0, filed on Feb. 27, 2017 and published as EP 3419998 on Jan. 2, 2019 (Applicant—The Board of Regents of the University of Texas System) (10 Pages).

Extended European Search Report dated Mar. 29, 2017 by the European Patent Office for Patent Application No. 14838354.0, which was filed on Aug. 21, 2014 and published as EP 3036005 on Jun. 29, 2016 (Inventor—Jiang et al.; Applicant—Applicant—Board of Regents, Univ. of Texas System) (3 pages).

International Search Report and Written Opinion dated Dec. 19, 2014 by the International Searching Authority for Patent Application No. PCT/US2014/052206, which was filed on Aug. 21, 2014 and published as WO 2015/027120 on Feb. 26, 2015 (Inventor—Jiang et al.; Applicant—Applicant—Board of Regents, Univ. of Texas System) (9 pages).

International Preliminary Report on Patentability dated Feb. 23, 2016 by the International Searching Authority for Patent Application No. PCT/US2014/052206, which was filed on Aug. 21, 2014 and published as WO 2015/027120 on Feb. 26, 2015 (Inventor—Jiang et al.; Applicant—Applicant—Board of Regents, Univ. of Texas System) (7 pages).

International Search Report and Written Opinion dated Jul. 17, 2017 by the International Searching Authority for Patent Application No. PCT/US2017/019605, which was filed on Feb. 27, 2017 and published as WO 2017/147561 on Aug. 31, 2017 (Inventor—Jiang et al.; Applicant—Board of Regents, Univ. of Texas System) (17 pages).

Issue Notification dated Feb. 21, 2018 by the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (1 page).

Non-Final Office Action dated Apr. 5, 2017 by the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (9 pages).

(56) References Cited

OTHER PUBLICATIONS

Notice of Allowance dated Oct. 23, 2017 by the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (7 pages).

Notice of Allowance dated Dec. 12, 2017 by the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (4 pages).

Office Action dated Dec. 4, 2019 by the SIPO for CN Application No. 201480056187.5, filed on Aug. 21, 2014 and published as CN 106659909 on May 10, 2017 (Applicant—Board of Regents of the University of Texas System) (Original—5 Pages // Translation—8 Pages).

Preliminary Amendment filed on Feb. 19, 2016 with the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (3 pages).

Preliminary Amendment filed on Aug. 4, 2016 with the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (5 pages).

Response to Non-Final Office Action filed on Oct. 5, 2017 with the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (94 pages).

Response to Restriction Requirement filed on Mar. 9, 2017 with the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (5 pages).

Restriction Requirement dated Nov. 9, 2016 by the U.S. Patent and Trademark Office for U.S. Appl. No. 14/912,986, filed Feb. 19, 2016 and issued as U.S. Pat. No. 9,914,775 on Mar. 13, 2018 (Inventor—Jiang et al.; Applicant—Board of Regents, Univ. of Texas System) (6 pages).

Office Action dated Jun. 26, 2020 by the EPO for EP Application No. 17 757 405.0-1110, filed on Feb. 27, 2017 and published as EP 3419998 on Jan. 2, 2019 (Applicant—Board of Regents of the University of Texas System) (6 Pages).

1 Cx43 cKO mice had tumor spread to the lungs, and 1 Cx43 cKO mouse had tumor spread to the lungs and brain

CX43 HEMICHANNEL ANTIBODIES AND METHODS OF USE

CROSS-REFERENCE TO RELATED PATENT APPLICATIONS

This application is a continuation of U.S. application Ser. No. 15/891,802 (now U.S. Pat. No. 10,633,442) filed Feb. 8, 2018, which is a continuation of U.S. application Ser. No. 14/912,986 (now U.S. Pat. No. 9,914,775), filed Feb. 19, 2016, which is a U.S. national phase application of International Application No. PCT/US2014/052206, which was filed Aug. 21, 2014, and which claims the benefit of priority to U.S. Provisional Application No. 61/868,112, filed on Aug. 21, 2013. The content of these earlier filed applications is hereby incorporated herein by reference.

SEQUENCE LISTING

The Sequence Listing submitted herewith as a text filed named "21105_0048U4_Sequence_Listing.txt," created on Mar. 18, 2020, and having a size of 11,241 bytes is hereby incorporated by reference pursuant to 37 C.F.R. § 1.52(e)(5).

BACKGROUND

Bone tissues are a preferred site of breast and prostate cancer metastasis. Bone metastasis occurs in up to 75% of patients with advanced cancers. Currently, there is no cure for metastatic breast cancer and no reliable intervention drug for treating bone metastasis that has minimal side effects.

Osteoarthritis (OA) is a prevalent disease that affects approximately 20% of U.S. adults. This disease causes the degeneration of joints including articular cartilage and subchondral bone. The pathology of OA is characterized by a loss of articular cartilage leading to narrowing of joint space, increased joint friction and potential structure remodeling. Current treatment includes exercise, lifestyle change and analgesics. If symptom becomes severe, joint replacement surgery is normally performed. Thus far, there is no specific pharmaceutical intervention available for the treatment of OA.

Connexin hemichannels play important roles in the cell and tissue function, and abnormal function of connexin hemichannels is known to cause various pathological conditions. Thus, there remains a need for additional therapies for treating pathological conditions associated with hemichannels activity (e.g., inflammation, osteoarthritis, or bone metastasis), as well as methods for identifying such therapies.

SUMMARY

The inventors have discovered that open hemichannels in cells of metastatic targets have inhibitory effects on cancer growth, migration, and metastasis. Certain embodiments provide a tool and/or method to identify compounds that modulate opening of hemichannels for the treatment of cancer metastasis. In certain aspects the drugs can be used to inhibit or ameliorate cancer metastasis to the bone, brain, or liver. In certain aspects a hemichannel can be expressed in a bone, brain, or liver cell. In a further aspect the hemichannel can be an osteocyte hemichannel, a hepatocyte hemichannel, or an astrocyte hemichannel. In certain aspects a hemichannel can be a connexin Cx43, Cx32, Cx46, Cx37, Cx40, Cx50, Cx59, Cx62, Cx26, Cx31, Cx30.3, Cx31.1, Cx30, Cx25, Cx45, Cx47, Cx30.2, Cx36, Cx31.9, Cx39, Cx40.1, Cx23, or Cx29 hemichannel. In certain aspect the hemichannel is a Cx43 or Cx 32 hemichannel. As an example, opening of connexin 43 (Cx43) hemichannels in osteocytes has an inhibitory effect on metastasis to the bone and can suppress bone metastasis.

Hemichannel opening can be detected by dye uptake assays using fluorescence dyes like Lucifer yellow, ethidium bromide, ALEXA 350, ALEXA 485, ALEXA 594 dyes, etc. The specificity of the hemichannel opening can be verified by using a Connexin specific antibody that inhibits hemichannel opening and thus inhibits the activity of the target reagent. Therefore, the tools and/or methods described can be used for screening, testing, and identifying reagent(s) that open hemichannels and inhibit metastasis.

Certain embodiments are directed to methods of identifying a compound that open hemichannels. Other embodiments are directed to methods of positively modulating the opening of hemichannels in to inhibit or ameliorate cancer metastasis.

The present invention provides antibodies directed against a hemichannel, nucleic acids encoding such antibodies and therapeutic proteins, methods for preparing anti-hemichannel monoclonal antibodies and other therapeutic proteins, and methods for the treatment of diseases, such as metastatic cancer. In certain aspects the antibody binds an epitope having an amino acid sequence of FLSRPTEKTI (SEQ ID NO: 13), KRDPCPHQVD (SEQ ID NO:14), or LSAVYTCKR (SEQ ID NO:15). In a particular aspect an antibody binds an epitope having an amino acid sequence of FLSRPTEKTI (SEQ ID NO: 13).

In one embodiment, the invention provides an isolated antibody which specifically binds to hemichannels, comprising a heavy chain having an amino acid sequence of SEQ ID NO:2 and a light chain having an amino acid sequence of SEQ ID NO:4.

In certain aspects a first heavy chain region comprises an amino acid sequence having an amino acid sequence of residues 13 to 37 of SEQ ID NO:2; a second heavy chain region having an amino acid sequence corresponding to residues 46 to 66 of SEQ ID NO:2; and a third heavy chain region comprising an amino acid sequence having an amino acid sequence of residues 97 to 116 of SEQ ID NO:2.

In another aspect a first light chain region comprises an amino acid sequence having an amino acid sequence of residues 9 to 40 of SEQ ID NO:4; a second light chain region having an amino acid sequence corresponding to residues 49 to 58 of SEQ ID NO:4; and a third light chain region comprising an amino acid sequence having an amino acid sequence of residues 64 to 108 of SEQ ID NO:4.

In one embodiment, the invention provides an isolated antibody which specifically binds to hemichannels and gap junctions, comprising a heavy chain having an amino acid sequence of SEQ ID NO:6 and a light chain having an amino acid sequence of SEQ ID NO:8.

In certain aspects a first heavy chain region comprises an amino acid sequence having an amino acid sequence of residues 13 to 37 of SEQ ID NO:6; a second heavy chain region having an amino acid sequence corresponding to residues 46 to 66 of SEQ ID NO:6; and a third heavy chain region comprising an amino acid sequence having an amino acid sequence of residues 97 to 116 of SEQ ID NO:6.

In another aspect a first light chain region comprises an amino acid sequence having an amino acid sequence of residues 9 to 42 of SEQ ID NO:8; a second light chain region having an amino acid sequence corresponding to residues 51 to 60 of SEQ ID NO:8; and a third light chain region comprising an amino acid sequence having an amino acid sequence of residues 66 to 125 of SEQ ID NO:8.

In one embodiment, the invention provides an isolated antibody which specifically binds to gap junctions, comprising a heavy chain having an amino acid sequence of SEQ ID NO: 10 and a light chain having an amino acid sequence of SEQ ID NO: 12.

In certain aspects a first heavy chain region comprises an amino acid sequence having an amino acid sequence of residues 10 to 34 of SEQ ID NO: 10; a second heavy chain region having an amino acid sequence corresponding to residues 43 to 59 of SEQ ID NO: 10; and a third heavy chain region comprising an amino acid sequence having an amino acid sequence of residues 94 to 109 of SEQ ID NO: 10.

In another aspect a first light chain region comprises an amino acid sequence having an amino acid sequence of residues 9 to 40 of SEQ ID NO: 12; a second light chain region having an amino acid sequence corresponding to residues 49 to 58 of SEQ ID NO: 12; and a third light chain region comprising an amino acid sequence having an amino acid sequence of residues 64 to 108 of SEQ ID NO: 12.

In certain aspects antibodies include full length antibodies, antibody fragments, single chain antibodies, bispecific antibodies, minibodies, domain antibodies, synthetic antibodies and antibody fusions, and fragments thereof.

A further embodiment provides a pharmaceutical composition comprising an antibody as described herein with a pharmaceutically acceptable carrier. Also provided is an antibody or a pharmaceutical composition of the invention for use as a medicament or for use in therapy for cancer and to inhibit cancer metastasis.

A further embodiment provides a method of treating or preventing cancer metastasis. A method of treating can comprise administering to a subject in need thereof an effective amount of an isolated antibody described herein. Also provided is the use of an antibody as described herein in the manufacture of a medicament for the treatment or prevention of cancer metastasis.

Certain aspects are directed to in vitro methods of using an antibody, compounds or reagents to suppress inflamatory reactions in chondrocytes. In certain aspects methods are directed to determining the effect on inhibition of Cx43 hemichannel opening in chondrocytes by (i) determining hemichannel opening by dye uptake assay, using Lucifer yellow or Alexa dyes, (ii) assessing inhibitory effects on hemichannels opening by IL-1β, (iii) test inhibitory effects of the reagents on hemichannels opening by mechanical loading in the form of fluid flow shear stress.

Certain aspects are directed to methods of determining the effect of an antibody, compounds or reagents on suppressing of inflammatory responses evoked by IL-1β and mechanical loading by (i) determining the inhibition of activation of nuclear factor-kappaB (NF-κB) induced by IL-1β, (ii) determining the inhibition of activation of NF-κB induced by fluid flow shear stress.

Other aspects are directed to an in vivo method of using a monoclonal antibody, compounds or reagents to treat OA or identify the same comprising (i) injecting antibody, compound or reagent into knee cap cavity, (ii) assessing the inhibition of activation of NF-κB induced by IL-1β, (iii) assessing OA development by X-ray, histological analysis and physical movement.

As used herein, the term "antigen" is a molecule capable of being bound by an antibody or T-cell receptor. In certain embodiments, binding moieties other than antibodies and be engineered to specifically bind to an antigen, e.g., aptamers, avimers, and the like.

The term "antibody" or "immunoglobulin" is used to include intact antibodies and binding fragments/segments thereof. Typically, fragments compete with the intact antibody from which they were derived for specific binding to an antigen. Fragments include separate heavy chains, light chains, Fab, Fab' F(ab')2, Fabc, and Fv. Fragments/segments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes bispecific antibodies. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin Exp Immunol* 79:315-21, 1990; Kostelny et al., *J. Immunol.* 148:1547-53, 1992.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation."

The term "providing" is used according to its ordinary meaning "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The phrase "specifically binds" or "specifically immunoreactive" to a target refers to a binding reaction that is determinative of the presence of the molecule in the presence of a heterogeneous population of other biologics. Thus, under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane, Antibodies: A Laboratory Manual, Cold Spring Harbor Press, 1988, for a description of immunoassay formats and conditions that can be used to determine specific immunoreactivity.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

Cells were allowed to attach for 90 min. The cells were examined under a fluorescence microscope.

Figure 16:
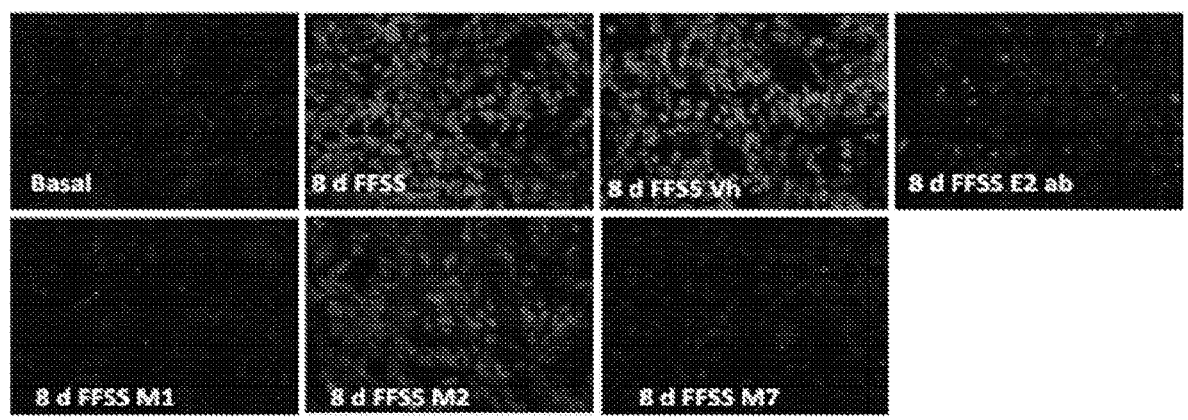

FIG. 16. Shows blockage of hemichannel opening induced by mechanical loading by M1 and M7, but not M2. MLO-Y4 cells were pretreated with or without mAbs for 20 min. The cells were subjected to fluid flow shear stress at 8 dynes/cm$^2$ for 10 min and dye uptake was performed with 100 µM EtBr for 5 min. Cells were rinsed, fixed and images were taken under fluorescence microscopy.

Figure 17:
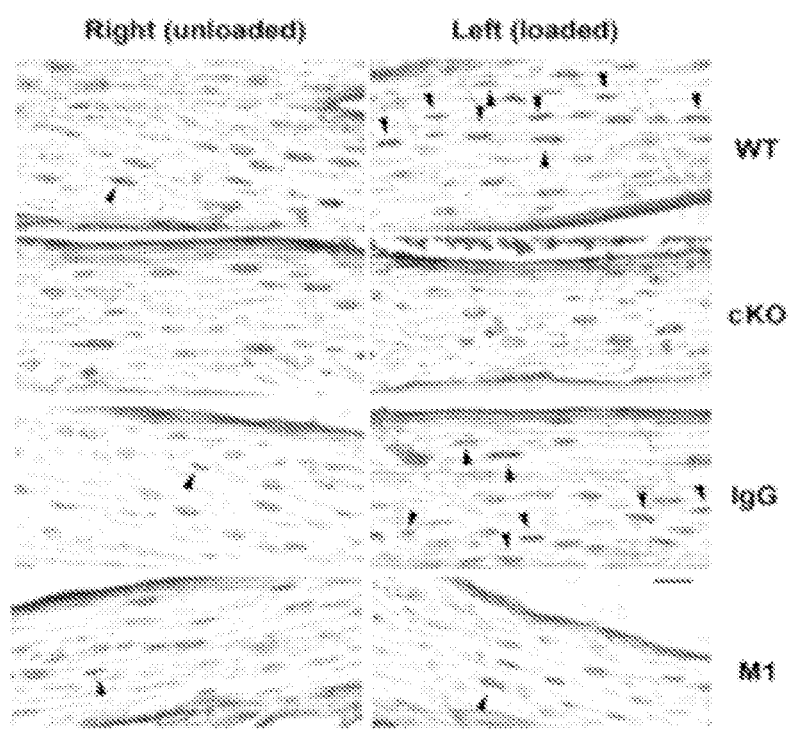

FIG. 17. Shows that M1 blocks hemichannel opening induced by mechanical loading in mouse bone osteocytes in vivo. Mouse IgG or Cx43(M1) mAb (25 mg/kg) was injected 2 hr before Evans blue dye injection Into WT and Cx43 cKO mice. 30 min after dye injection, left (L) tibias were mechanically loaded once for 10 min. Mice were euthanized and perfused with 50 ml PBS. Tibias were isolated and fixed and bone tissue sections were prepared. Bar, 40 mm. The arrowheads indicate dye uptake.

Figure 18:
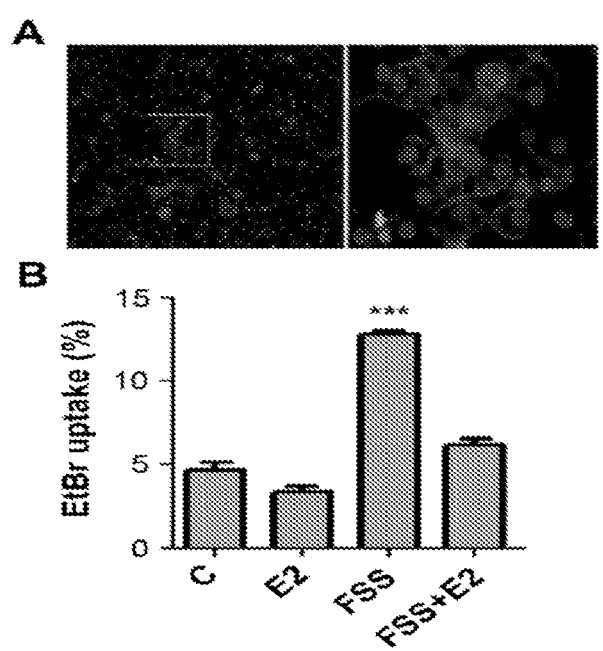

FIG. 18. Shows expression of Cx43 on the surface of chondrocytes. (A) Expression of Cx43 on the surface of primary chondrocytes. (B) Fluid flow shear (16 dynes/cm2) (FSS) opened hemichannels and this opening was significantly blocked by Cx43 specific antibody. FSS compared to all other conditions, ***, P<0.001.

DESCRIPTION

Various cells are able to communicate with each other and with the extracellular environment through hemichannels and gap junctions formed by the protein connexin. Connexin proteins are ubiquitously expressed throughout the body. Six connexin proteins make up one hemichannel, and 2 hemichannels make up 1 gap junction channel. Gap junctions are a cluster of channels that are located in the plasma membrane between adjoining cells and they mediate intercellular communication. Hemichannels are a separate entity from gap junction channels. Hemichannels permit the exchange of molecules between the intracellular compartments and the extracellular environment.

Osteocytes express hemichannels known as connexin (Cx) 43 hemichannels. These osteocyte hemichannels are normally closed and can be opened when exposed to mechano-stimulation, which leads to the release of various factors into the bone microenvironment. The factors released by hemichannel opening can mediate other processes that can decrease tumor cell migration and bone metastasis.

Certain embodiments are directed to methods of identifying reagents that modulate the opening of connexin hemichannels. In certain aspects the methods identify compounds or drugs that positively modulate the opening of connexin hemichannels. Other embodiments are directed to methods of treating cancer by administering a compound that open hemichannels to a patient having cancer. In certain aspects the patient has a primary tumor. In certain aspects compounds that open Cx43 hemichannels can be used to inhibit or reduce metastasis to the bone.

Cancer metastasis occurs when a cancer spreads from the part of the body where it originated (e.g., breast or prostate) to other parts of the body (e.g., liver or bone) and establishes a secondary tumor. The bone is one of the most common sites of cancer metastasis. Cancers that metastasize to bone include, but are not limited to breast cancer, prostate cancer, lung cancer, and skin cancers (e.g., melanoma). Bone metastasis can be identified in up to 75% of patients with advanced breast and prostate cancers. Bone metastasis (mets) are associated with many significant clinical and quality of life consequences, such as, but not limited to intractable pain, pathological fractures, spinal cord and nerve compression, bone marrow infiltration, and impaired motility. In many cases the systemic presence of a cancer can also make the cancer incurable.

Normal bone is made up of three major cell types: bone-forming osteoblasts, bone-resorbing osteoclasts, and osteocytes. Osteocytes make up approximately 95% of bone cells and maintain the bone remodeling process by coordinating osteolytic and osteoblastic activities. When cancer cells invade the bone, many of the normal bone functions are affected. Cancer cells interact with the local microenvironment to promote cancer cell survival via bone destruction and vascularization.

Cx43 hemichannels in osteocytes have been shown to open by treatment with alendronate (AD), an efficacious and commonly used bisphosphonate drug. Bisphosphonates are a class of drugs known for treating many bone disorders including bone metastasis. Powles et al. have shown administration of bisphosphonates to be associated with a decrease in the incidence of bone metastasis and a decrease in death rate in patients with breast cancer. AD has been associated with decreased tumor growth as well as reduced bone destruction and pain. AD inhibits osteoclast activity and induces the opening of Cx43 hemichannels in osteocytes (Plotkin et al., 2002). However, AD administration is accompanied by multiple, severe side-effects.

I. Methods Related to the Screening of Drug Candidates as Suppressors of Bone Metastasis A. In Vitro Assays Certain embodiments are directed to detection of hemichannel opening in vitro using a dye-uptake assay. In certain aspects the dye is a fluorescent tracer dye (e.g., ethidium bromide or Lucifer yellow).

Figure 1:
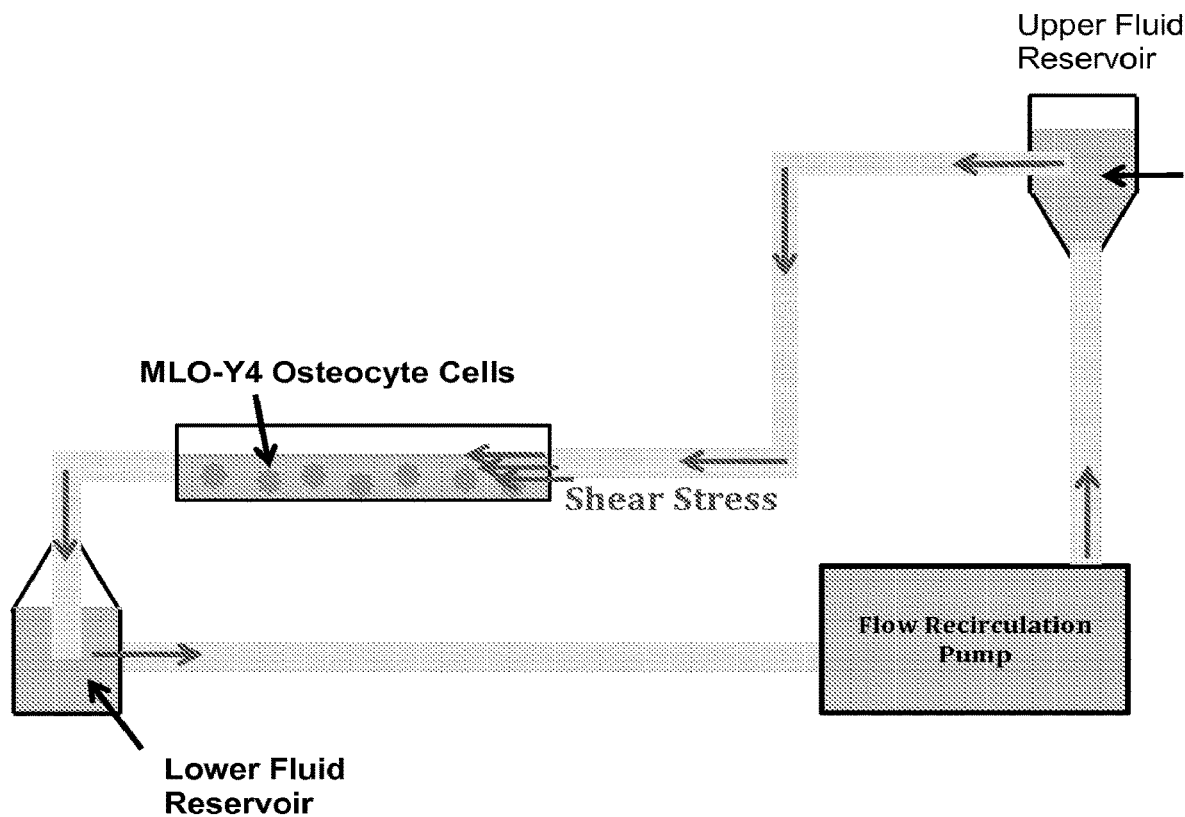
FIG. 1 illustrates one embodiment of a Fluid Flow Loop Apparatus.

In one example of an in vitro assay to detect hemichannel opening a fluid flow loop apparatus (FFLA) (Parallel Plate Flow Chamber), or modification thereof, can be used. One example of an FFLA apparatus is diagramed in FIG. 1. FFLA mimics dynamic fluid microenvironment in the bone to produce fluid flow shear stress (FFSS). Cells are cultured in a parallel plate flow chamber, exposing the cells to steady laminar fluid flow.

Osteocytes sense mechanical strain produced by FFSS in the osteocyte lacuna/canalicular network. It has been proposed that bone fluid flow is driven by extravascular pressure as well as applied cyclic mechanical loading of osteocytes and that the peak physiologic loads are 8 to 30 dyn/cm$^2$. In certain aspects FFSS levels were in range of physiological values reported from previous studies measuring fluid flow within bone. Fluid shear stress magnitude can be changed by adjusting column height of the flow loop.

Assays used to assess the functionality of the hemichannels can use a fluorescent tracer molecule that is small enough to pass through the pore of the hemichannel. If the hemichannel is closed the molecules cannot pass. If the hemichannel is open the dye can pass through and cause the cell to fluoresce, allowing quantification of the fluorescence. When ethidium bromide attaches to DNA it becomes fluorescent. Lucifer yellow fluoresces once it is located inside of a cell.

Dye transfer methods can comprise exposing cells to extracellular fluorescent permeability tracers. Extracellular permeability tracers are molecules that remain outside of cell unless some condition increases the permeability of the cell membrane. In certain aspects the tracers have a mass of less than 1, 2, or 3 kDa. In other aspect the tracer will have a net charge. Such permeability tracers include, but are not limited to the anionic dyes Lucifer yellow (LY; net charge=−1) and cationic probes ethidium bromide (Etd; net charge=+1), propidium iodide (PI; net charge=+2). The fluorescence of EtBr is enhanced upon binding to DNA, increasing the contrast and allowing more easy identification. In certain aspects extracellular dye is removed at different time periods or after the application of stimuli to open hemichannels and the fluorescence intensity retained by each cell is quantified. In certain aspects fluorescence intensity is quantified in snap shot images.

Figure 2:
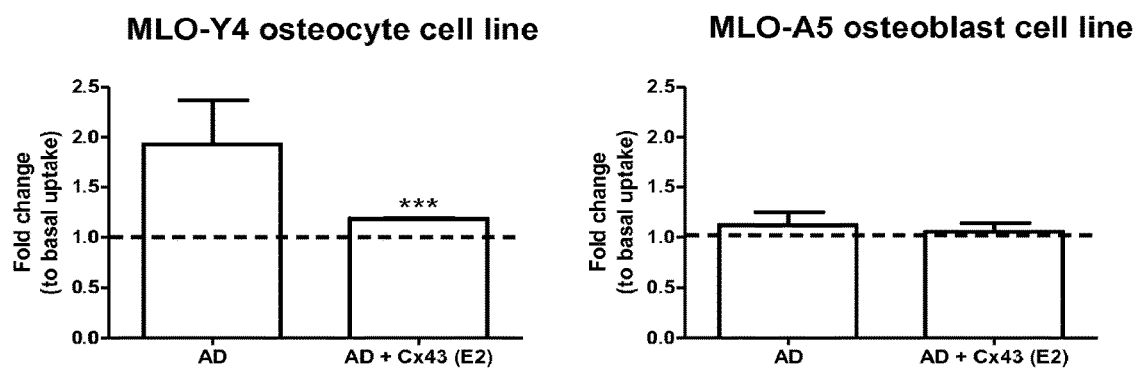
FIG. 2 illustrates results of treating MLO-Y4 osteocytic cells with 20 μM AD for 30 min in the absence or presence of 1 μg/ml Cx43(E2) antibody. Ethidium bromide dye uptake was conducted and quantified as compared to non-treated basal level of uptake. Study was carried out in calcium conditions. Low calcium conditions were used as control (opens hemichannels). Also illustrated are results of treating MLO-A5 osteoblasts with AD treatment or AD and Cx43(E2) antibody.

FIG. 2 illustrates the results from one example of an in vitro dye transfer assay. MLO-Y4 osteocytic cells were treated with 20 µM AD for 30 min in the absence or presence of 1 µg/ml Cx43(E2) antibody. Ethidium bromide dye uptake assay was conducted and quantified as compared to non-treated basal level of uptake. The assays were carried out in the presence of calcium. Low calcium conditions were used as a control (opens hemichannels). In addition MLO-A5 osteoblasts were treated with AD or AD plus Cx43(E2) antibody were used as negative controls—AD does not open Cx43 hemichannels in osteoblasts and opening of osteocytic hemichannels induced by AD is blocked by Cx43(E2) antibody.

The materials used in certain aspects of in vitro assays to identify positive modulators of hemichannels include:

Hemichannel expressing cells or cell lines. Cells or cell lines expressing the various connexin hemichannels can be obtained, isolated, or engineered using methods and/or expression vectors known in the art.

Osteocytes:

Primary osteocytes isolated from animals (including mouse, rats, rabbits, chicken) etc. or osteocytic cell lines including, but not limited to MLO-Y4 cells and others.

Cancer Cells:

Breast cancer cell lines: including ER, PR, HER and TP53 positive/negative cells (e.g., MD-MBA-231, MCF7, T47D, or ZR751). MDA-MB-231 is mammary gland ductal carcinoma. Py8119 mammary tumor cell lines were established from spontaneous mammary tumors arising in C57Bl/6 MMTV-PyMT females (mouse mammary tumor virus promoter-driven polyoma middle T transgene) mice. The expression of the oncogene (polyoma middle T transgene) is driven by the Mouse Mammary Tumor Virus promoter Prostate cancer cell lines: including androgen receptor and 5α-reductase positive/negative and androgen sensitive/insensitive cell lines (e.g., LNCaP-Rf, BM 18, pRNA-1-1/ras, RC58T/hTERT, PPC-1, etc).

Osteoblasts:

MLO-A5 osteoblasts are used as a control because they express Connexin 43, but they do not appear to open when stimulated by alendronate.

A "reagent" to be tested includes chemical compounds, peptides, proteins, antisense oligos, and/or microRNA.

Tracer Molecules include, but are not limited to lucifer yellow, ethidium bromide, Evans Blue, Alexa350, Alexa488 and Alexa594.

Cx43(E2):

The Cx43(E2) antibody is specific for Cx43 hemichannels. Cx43E2 binds the $2^{nd}$ extracellular loop of Cx43 hemichannels and prevents hemichannel opening.

Methods for determining if a reagent opens hemichannels include one or more of the following steps:

(a) Isolating, obtaining, or producing a connexin expressing cell or cell line. For example, isolating primary osteocytes from calveria. Other cell types can be isolated using other methods known in the art. In certain aspects calvarial osteocytes are isolated from animals (e.g., 16-day embryonic chicken calvaria or new-born mice). Animals are decapitated and calvarial bone is dissected and quickly dipped in 70% alcohol. The calvarial bone is then put in αMEM and washed multiple times with PBS. Cleaned bones are placed in fresh αMEM. The bones are minced and cut into 1.5 mm area size. The bone pieces can be treated with collagenase to remove soft tissues and osteoid followed by decalcification using EDTA. Finally, osteocytes are released from the bone chips by treating with collagenase and vigorous agitation.

(b) Isolating primary osteocytes from long bone. Long bone osteocytes can be isolated from 2-3 week old mice or rats. For example, mice are given an overdose of anesthesia, and cervically dislocated, decapitated, and dipped into 70% Ethanol. The femur and tibia with the end of the joints still intact are isolated. The leg is quickly dipped in 70% alcohol and then placed into αMEM. Legs in αMEM are washed with PBS. The major portion of muscle is removed, and detached from the tendons/ligaments. Cleaned bones are placed in fresh αMEM. Once all bones are cleaned, both ends of each bone are cut off using a scalpel just prior to flushing out the marrow using PBS. Bones are cut into 1.5 to 2 mm lengths and treated with collagenase. In one example, the bone pieces are treated with collagenase sequentially 9 times to remove all other tissues and osteoid followed by decalcification using EDTA.

(c) Culturing the cells or cell lines. For example, primary and/or osteocytic cell lines are cultured on collagen-coated plates and are bathed in recording medium ($HCO_3$-free α-MEM medium buffered with HEPES) containing a permeability tracer.

(d) Administering a test reagent. The cultured cells are placed contacted with a test reagent for desirable amount of time.

(e) Determining permeability tracer uptake. Permeability tracer uptake is determined by detecting the amount of tracer inside the cells. In certain aspects time-lapse recording is used. Fluorescence can be recorded at regions of interest in different cells with an eclipse filter on a microscope based on the wavelength of the fluorescence of the tracer or other probe(s) being used. In certain aspects images are captured by fast cooled digital camera every 2 minutes and image processing is performed with ImageJ software. The collected data can be illustrated as fold difference of initial fluorescence and fluorescence at the time of interest versus the basal fluorescence.

For snapshot images, cells can be exposed to permeability tracer for 5-10 minutes, rinsed multiple times with PBS, and fixed with formaldehyde. In certain aspects, at least three microphotographs of fluorescence fields are taken with a microscope. Image analysis is done with ImageJ software. The average of pixel density of random cells is measured.

In certain aspects the opening of connexin hemichannels is confirmed. Confirmation can be obtain by, for example, incubating osteocytes with Cx43(E2) antibody, a polyclonal antibody specifically inhibiting Cx43 hemichannels, along with the test reagent. If the reagent opens Cx43 hemichannel, this channel opening will be blocked by Cx43(E2) antibody. To control for the opening of Cx43 hemichannels, osteocytes are treated with fluid flow shear stress and/or AD, both known to open hemichannels in osteocytes.

In a particular example, MLO-Y4 osteocytic cells were treated with 20 µM AD for 30 min in the absence or presence of 1 µg/ml Cx43(E2) antibody. Ethidium bromide dye uptake was conducted and quantified as compared to non-treated basal level of uptake. The assay was carried out in presence of calcium. Low calcium conditions can be used as control (opens hemichannels). The opening of osteocytic hemichannels induced by AD is blocked by Cx43(E2) antibody.

Opening of Osteocytic Cx43 Hemichannels Mediate a Negative Effect on Cancer Cell Migration.

Figure 3:
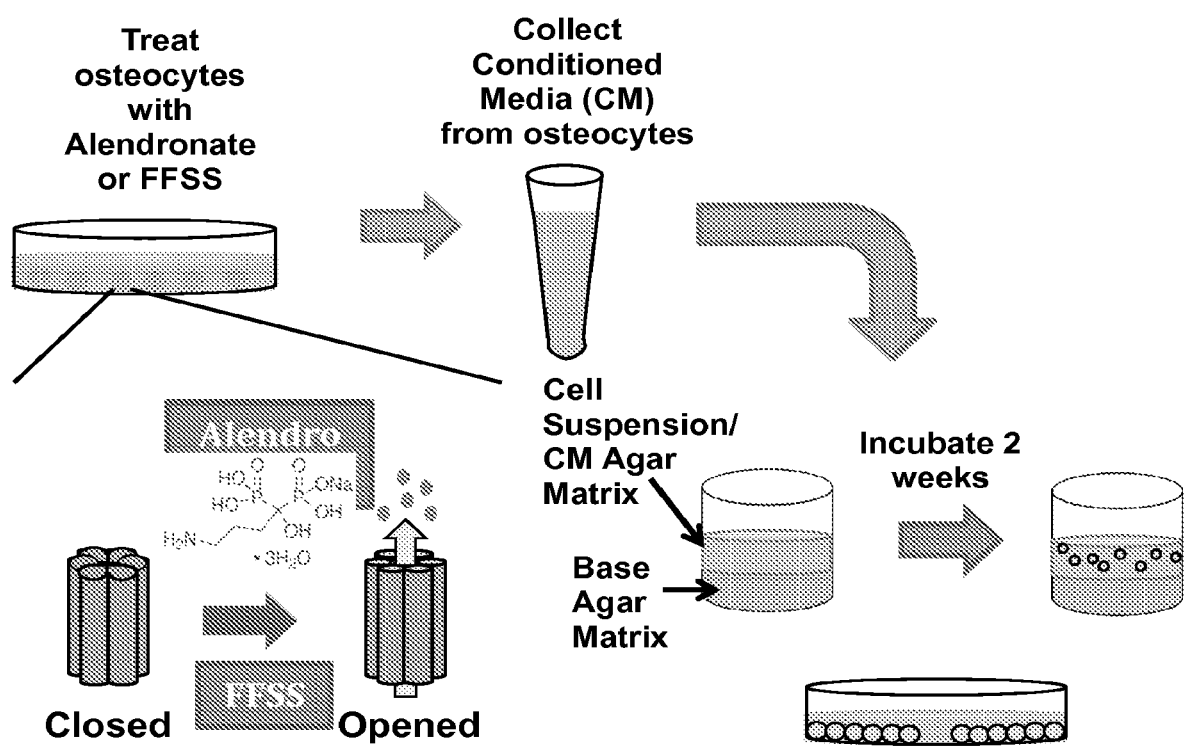
FIG. 3 illustrates a model system to study the role of osteocytic Cx43 hemichannels in mediating the effect of AD on cancer cell migration. Cx43 hemichannels in osteocytes are open by AD or FFSS. The released factor(s) in the AD- or FFSS-treated CM decreases cancer cell migration. Cancer cells treated with control CM exhibit normal migration.
Figure 4A:
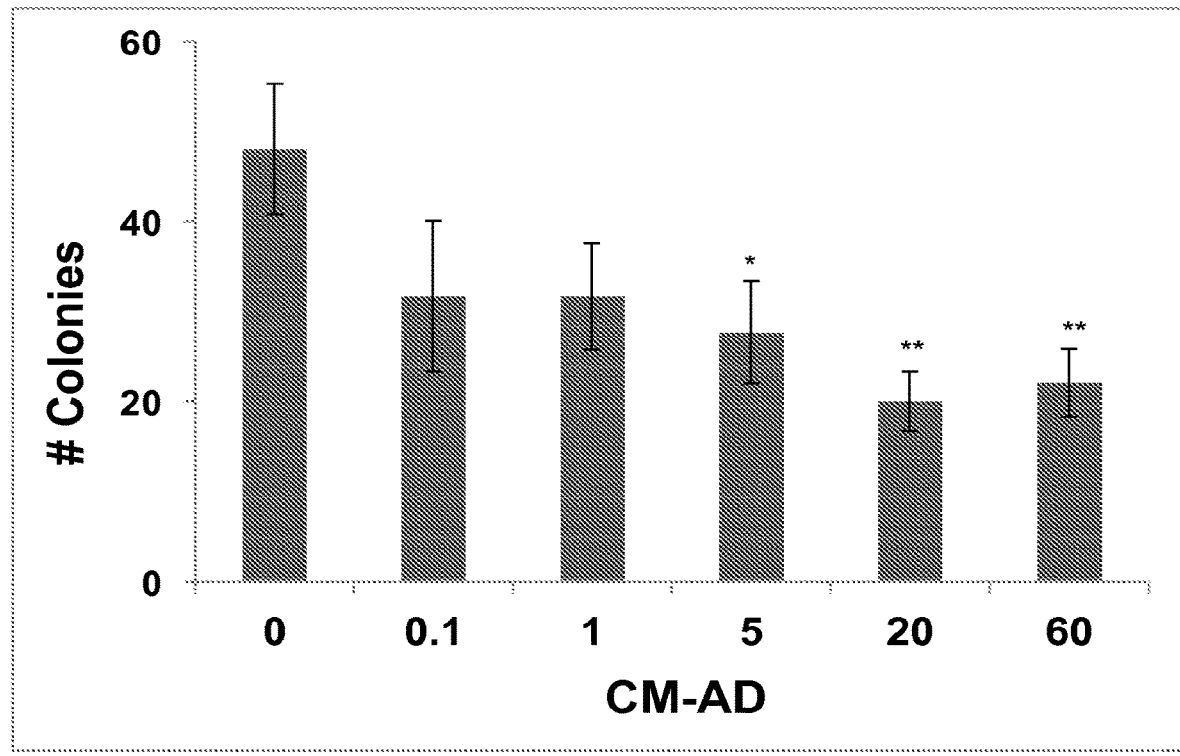
FIGS. 4A and 4B illustrate studies using a soft agarose anchorage-independent growth assay, which is different from anchorage-dependent growth. Only cancer cells can grow on soft agar and their growth on this matrix indicates the extent of the cancer cell proliferation. CM-AD from osteocytes decreases MDA-MB-231 colony formation.
Figure 4B:
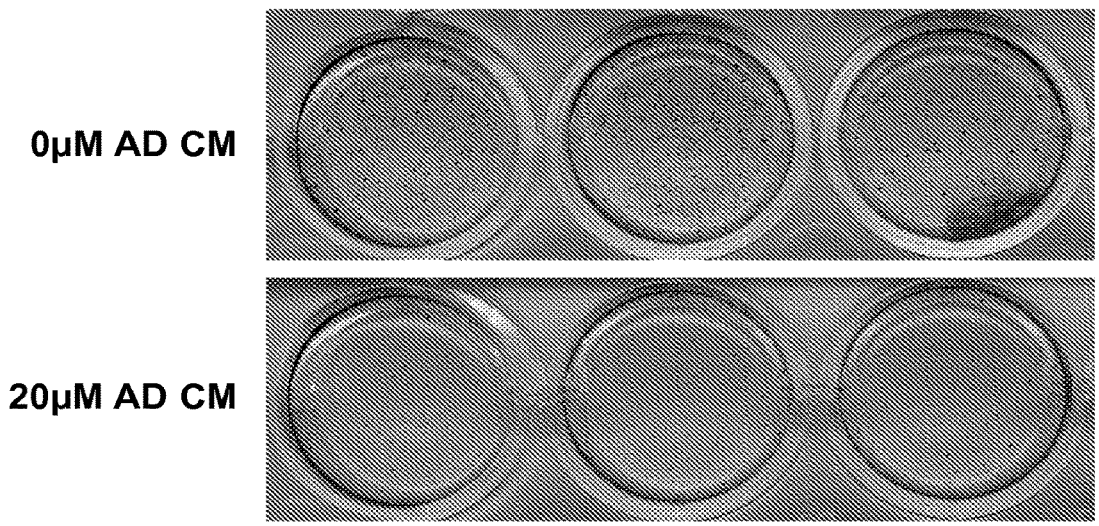
Figure 5A:
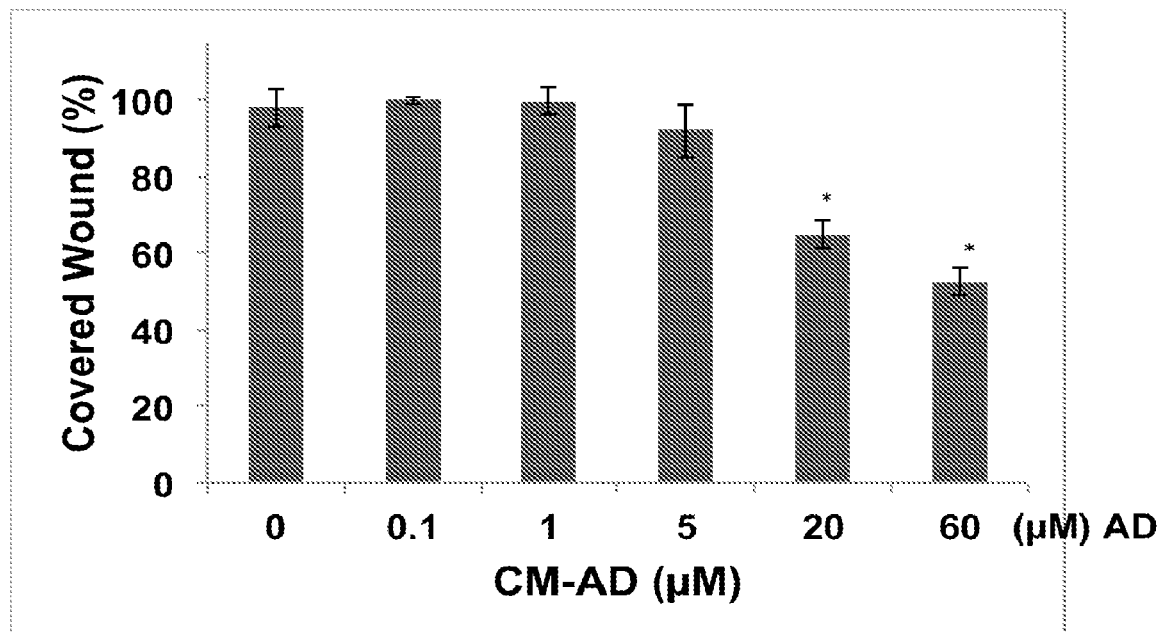
FIGS. 5A and 5B illustrate the results of studies using a wound healing migration assay. CM-AD from osteocytes inhibits MDA-MB-231 cell migration.
Figure 5B:
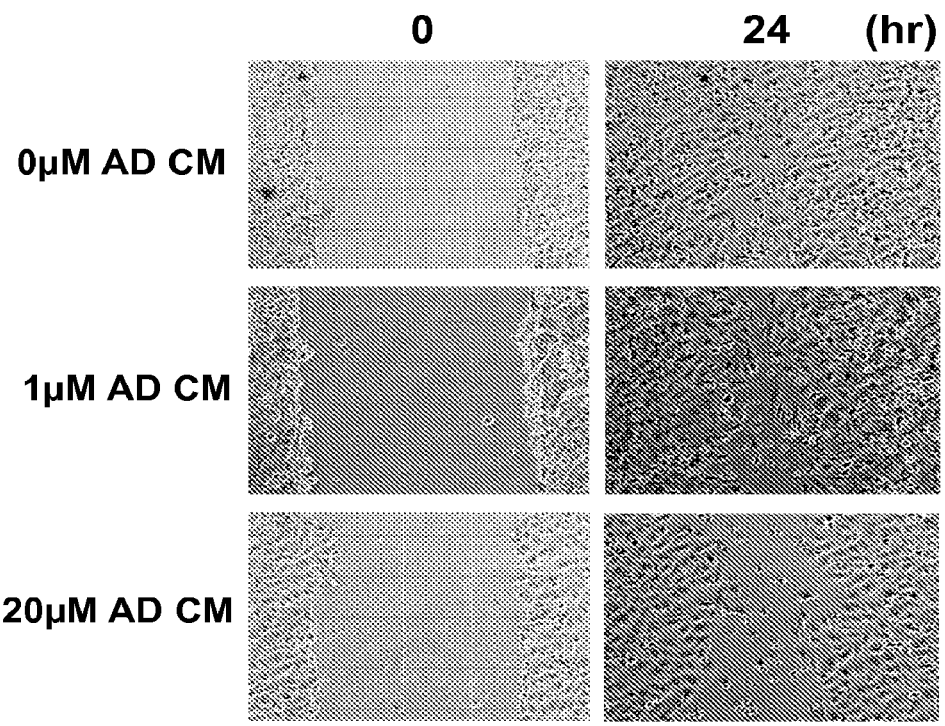
Figure 6:
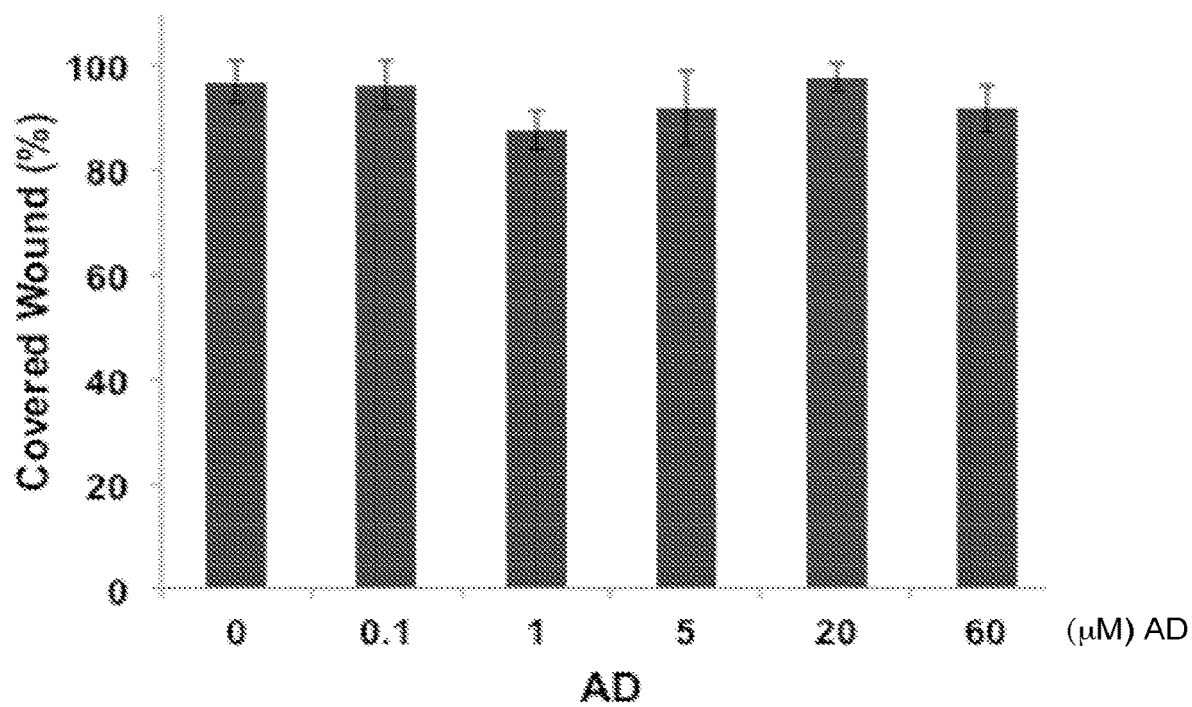
FIG. 6 illustrates results of another wound healing migration assay. AD does not have a direct effect on the migration of MDA-MB-231 cells.
Figure 7A:
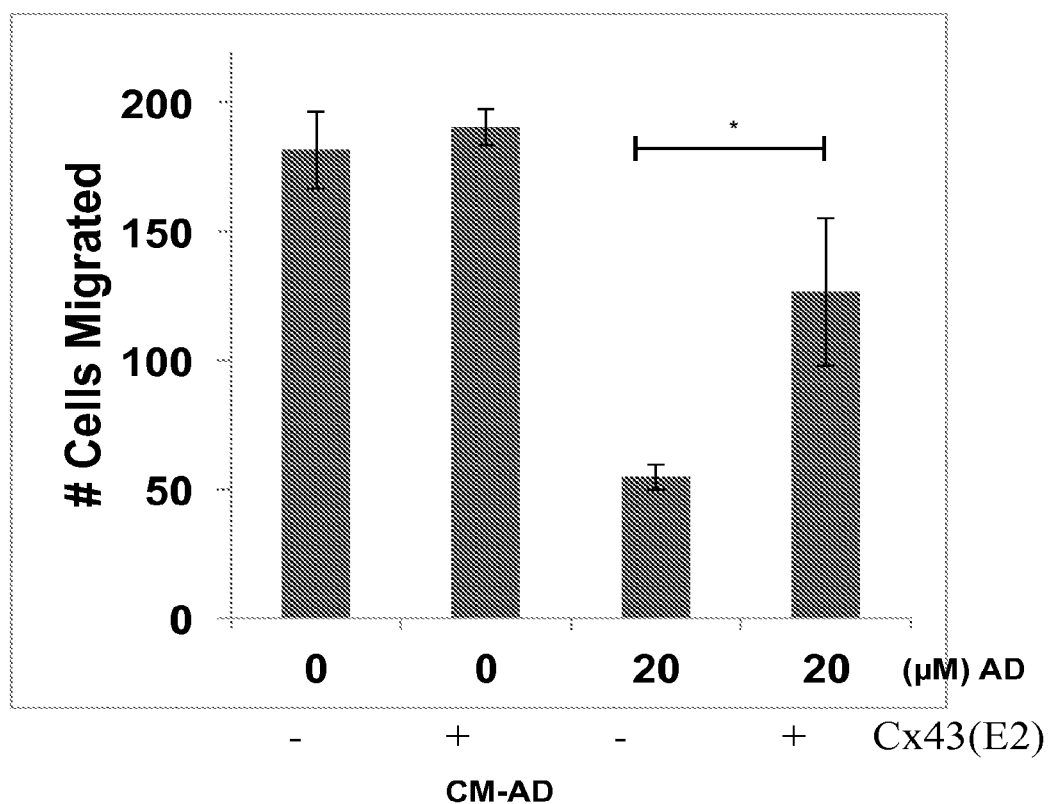
FIGS. 7A and 7B illustrate results from a transwell migration assay. (B) Dots represent the cells that have migrated to the opposite end of the insert and have been stained. The smaller dots are the pores through which they migrate. In this assay protein A was used to remove the E2 Ab from CM, and this causes the migration effect to be the same before E2 Ab was added.
Figure 7B:
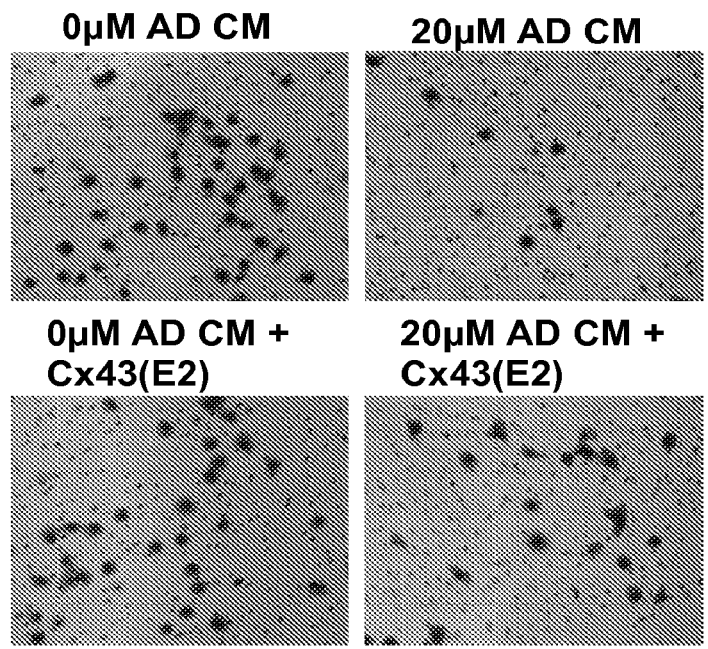
Figure 8:
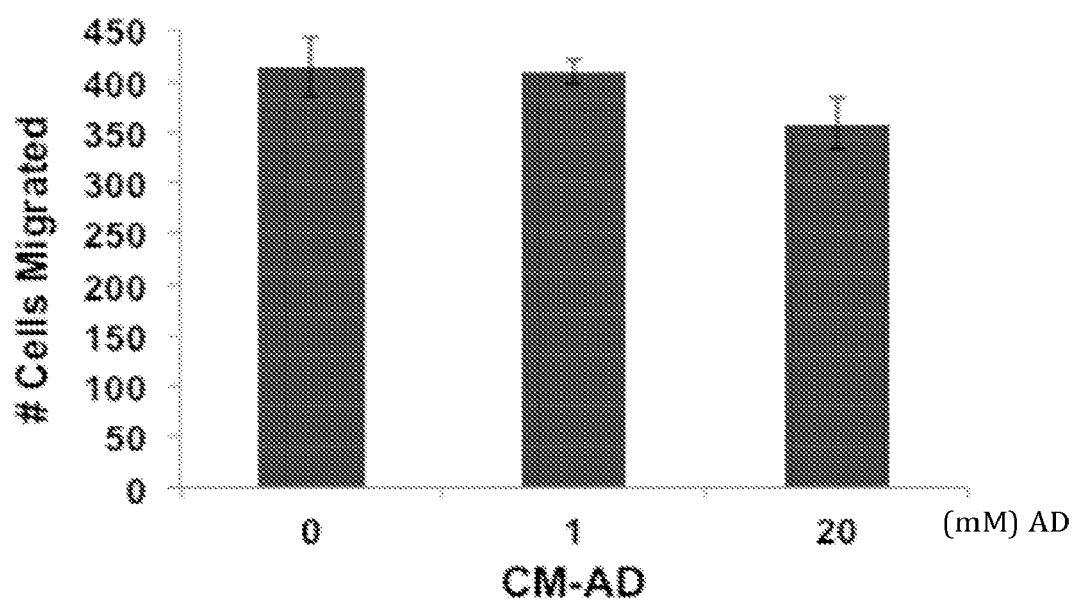
FIG. 8 illustrates results from another transwell migration assay. MDA-MB-231 migration is not affected by CM-AD from MLO-A5 osteoblasts.
Figure 9:
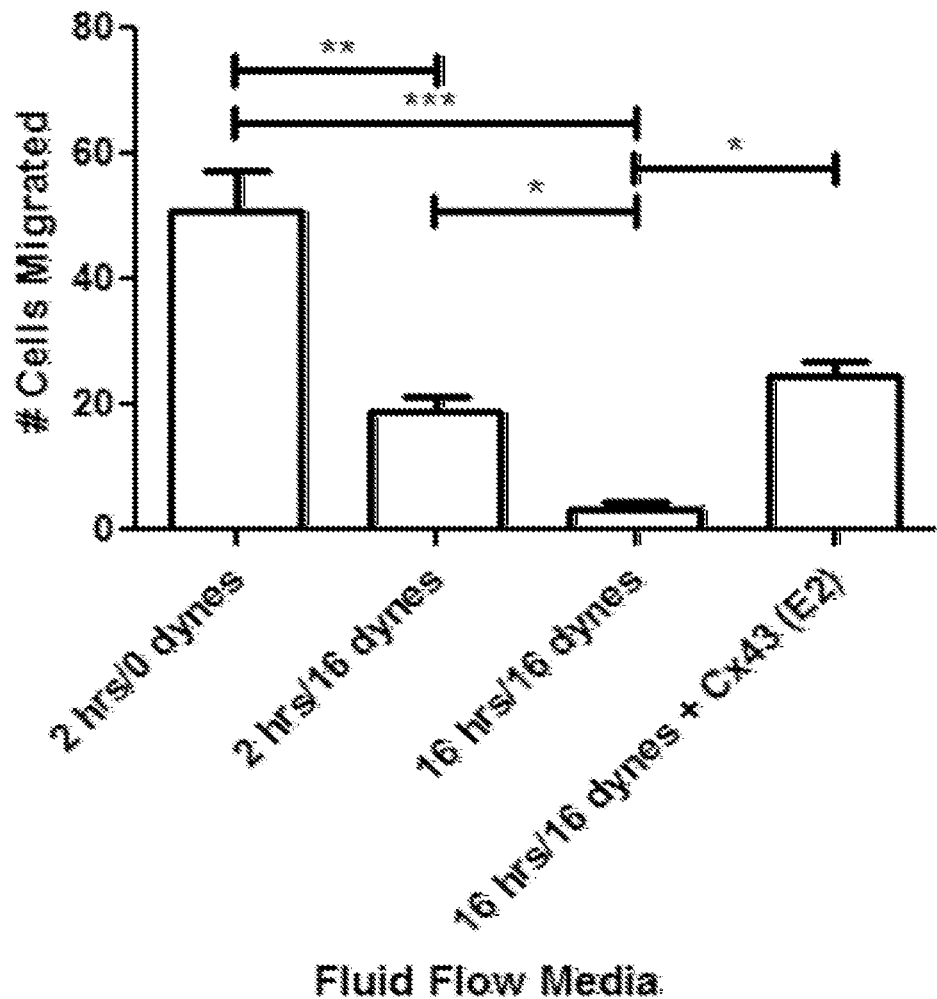
FIG. 9 illustrates results from another transwell migration assay. MDA-MB-231 migration is decreased with CM from osteocytes stimulated by mechanical loading.
Figure 10A:
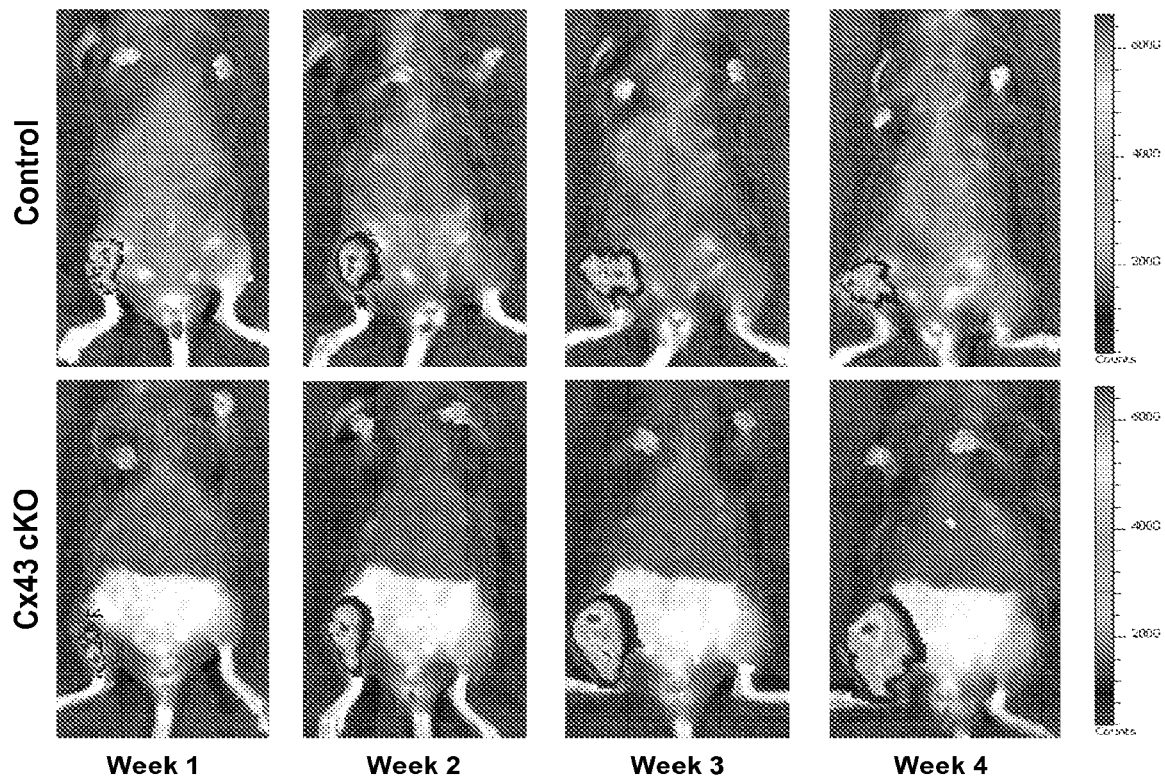
FIGS. 10A and 10B illustrate results from Py8119 breast cancer cell injection into Cx43 conditional knockout (cKO) mice. Py8199 tumor growth and metastasis is increased in Cx43 cKO mice. (B) Tumor spread to other tissues in Cx43 cKO mice.
Figure 10B:
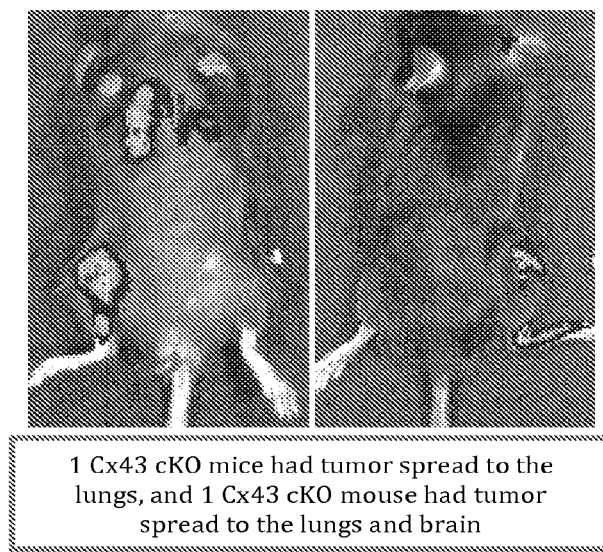
Figure 11:
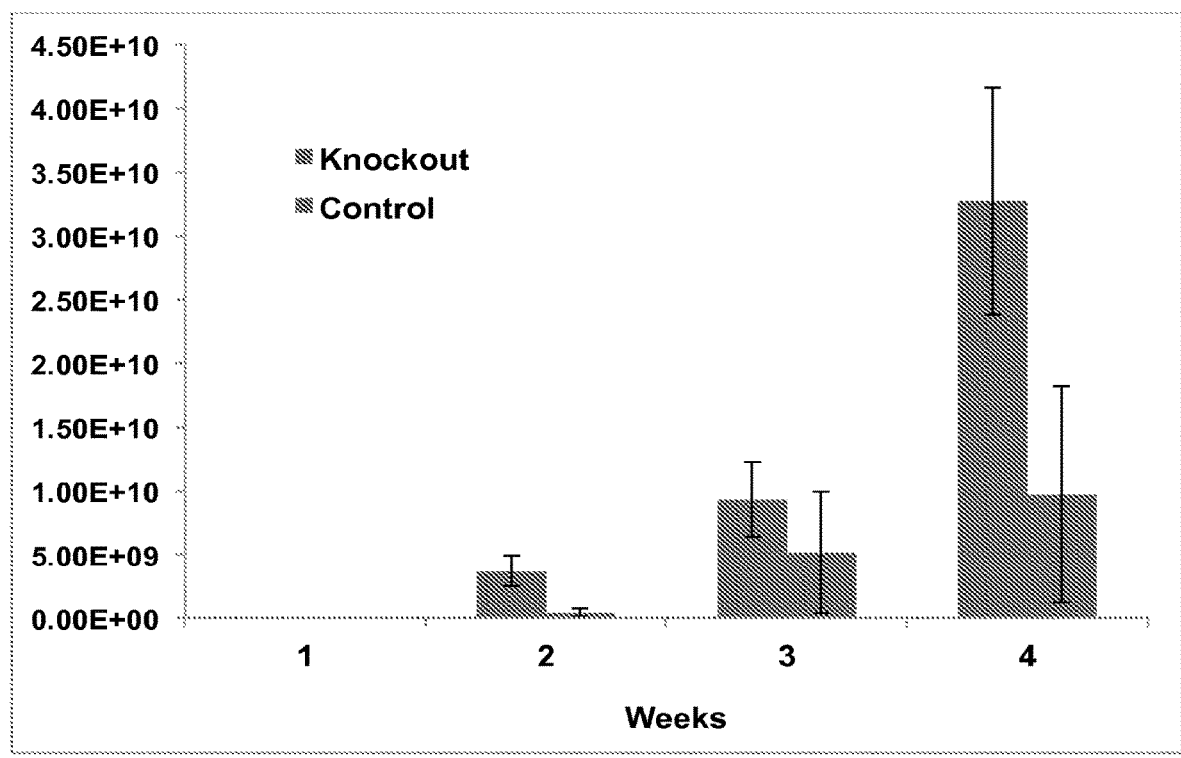
FIG. 11 illustrates results from Py8119 injection into Cx43 cKO mice. Py8119 tumor growth is increased in Cx43 cKO mice.
Figure 12:
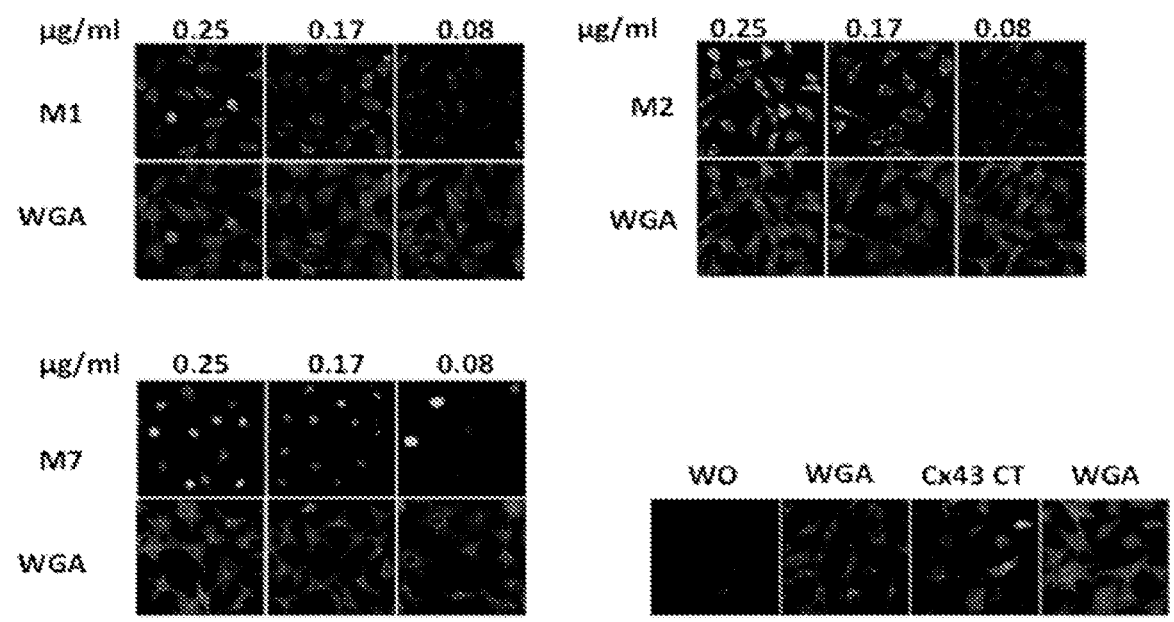
FIG. 12 illustrates immunolabeling of Cx43 by the three mAbs. Osteocyte MLO-Y4 cells were fixed with 70% ethanol at −20° C. for 20 min, blocked overnight, incubated with mAbs for 3 h RT at the concentrations shown above. Goat anti-mouse FITC secondary antibodies were used to assess the activities of these mAbs. WGA as a cell marker was labeled in red.
Figure 13:
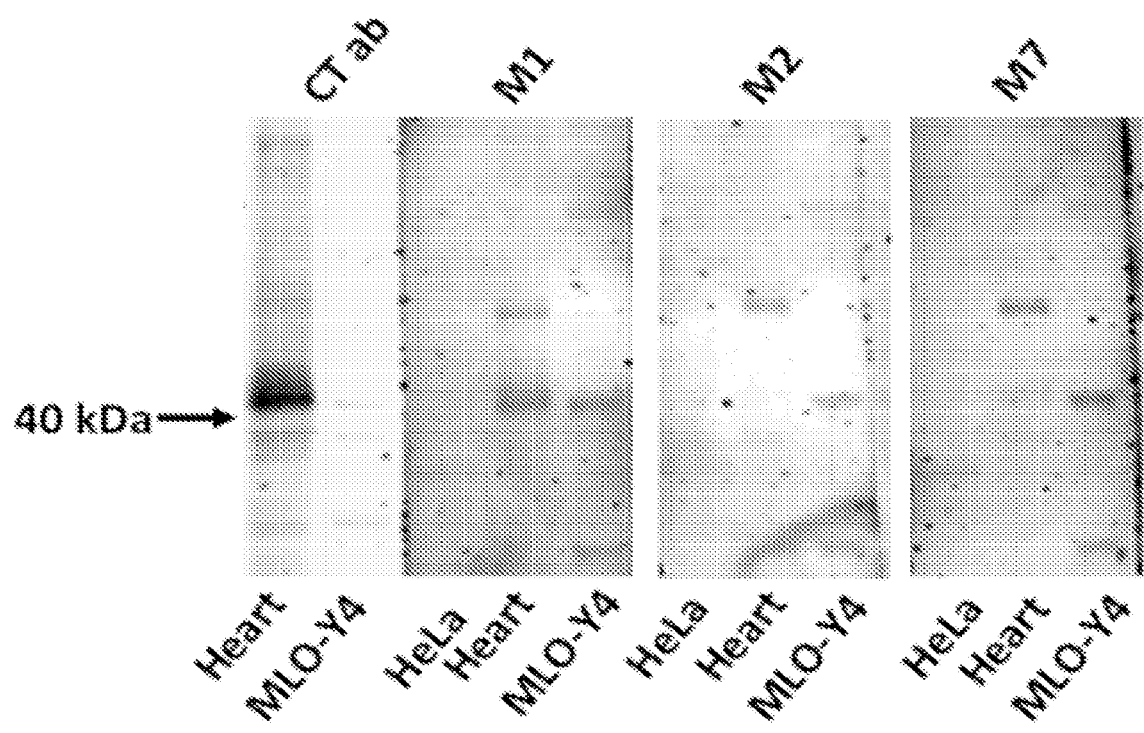
FIG. 13 shows hybridoma supernatants affinity purified by passing through Cx43 E2 column at pH 7.4. The western blots were performed with 1:100 dilution of each monoclonal antibody. Polyclonal Cx43 Ab dilution was 1:300.
Figure 14:
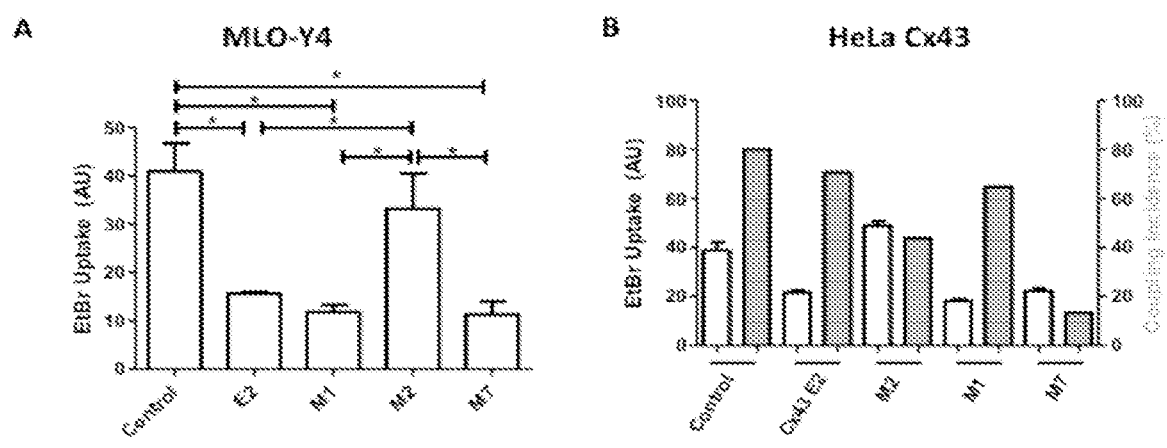
FIG. 14 shows that M1 blocks hemichannels, but not gap junctions; M2, blocks gap junctions, but not hemichannels; and M3 blocks both. (A) MLO-Y4 cells were incubated with media with low $Ca^{2+}$ and $Mg^{2+}$, a condition that induces the opening of Cx43 hemichannels. Dye uptake assay was performed in the presence of EtBr with or without mAbs for 20 min. (B) HeLa cells transfected with Cx43 were incubated with mAbs for 3 h and a signal cell was microinjected with AlexaFluor 488 to evaluate the extent of dye transfer assayed for gap junctions.
Figure 15:
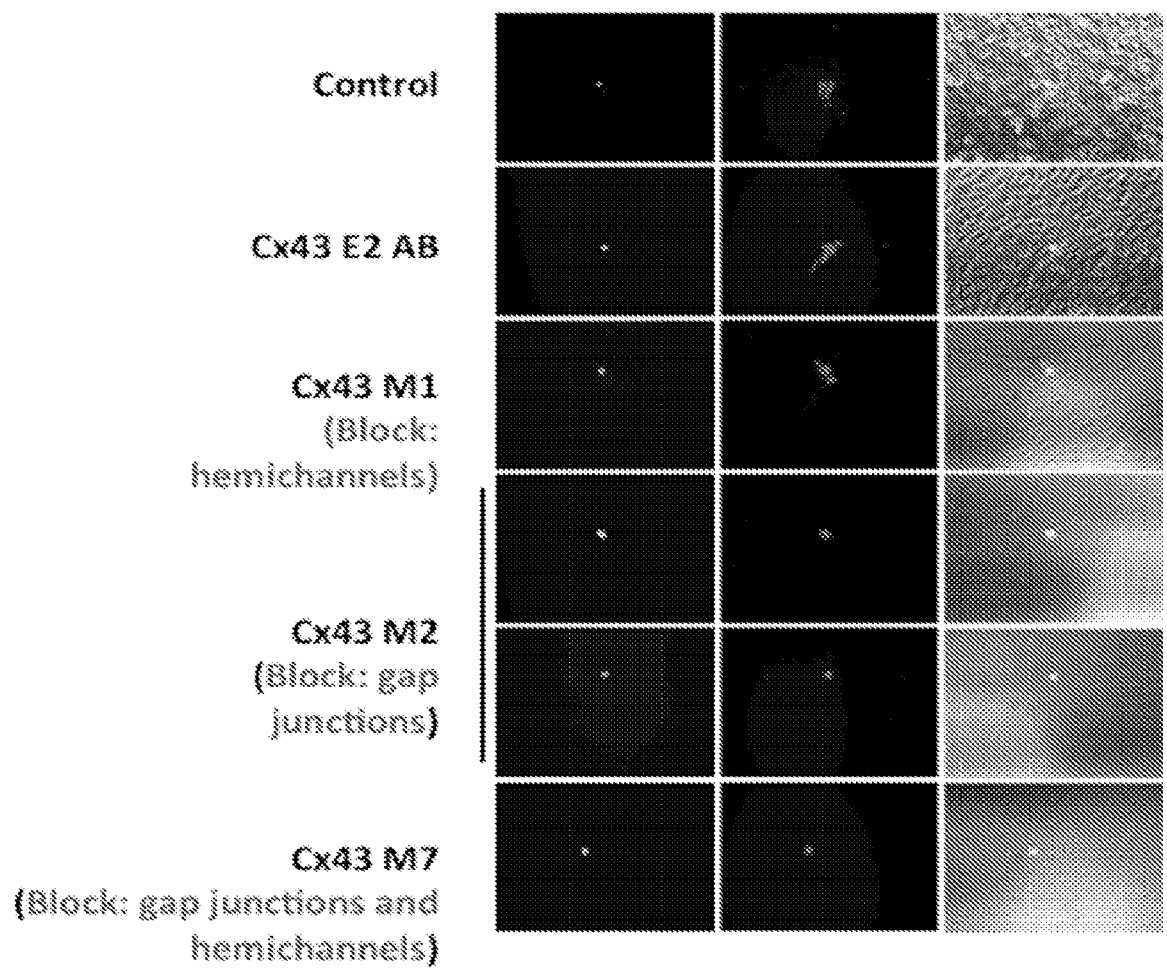
FIG. 15 illustrates parachuting dye transfer assay showing M2 and M7, but not M1 blocks gap junction channels. Hela cells transfected with Cx43 was used for parachuting dye transfer experiments. Donor cells were incubated with 5 μM calcein red-orange-AM (790 Da) which is permeable to gap junctions and 5 μM Oregon green 488 BAPTA-2-AM (1752 Da) which is non-permeable to gap junctions for 40 minutes at 37° C. Donor cells were treated with trypsin and separated preloaded cells were layered ('parachuted') over the top of the unlabeled recipient cells at a 1:4 donor to receiver ratio.

Cx43 hemichannels in osteocytes are opened by administration of AD or FFSS. The opened hemichannels permit the release of various factors into the medium producing a conditioned medium (CM). The released factor(s) in the AD- or FFSS-treated CM decrease cancer cell migration as determined by soft agar and wound healing assays. An example of a soft agar assay is diagrammed in FIG. 3. As illustrated in FIG. 4, cancer cells treated with control CM exhibit normal migration. The soft agar assay is an assay for anchorage-independent growth, as contrasted with anchorage-dependent growth. Only cancer cells can grow on soft agar and their growth on this matrix indicates the extent of the cancer cell proliferation.

In certain aspects the methods include incubating primary osteocytes or osteocyte cell lines with a test reagent in α-MEM for various periods of time and collecting the supernatant (conditioned media) at various time points. In certain aspects breast or prostate cancer cells are incubated with CM and cancer cell proliferation, migration, and invasion are determined.

Cancer cell growth and viability can be determined using WST-1 (Water Soluble Tetrazolium salts) assay, viable cell counting using Trypan blue method, BrdU DNA incorporation, and cell proliferation assay. For WST-1 assay, the cell proliferation is measured at an emission wavelength of 450 nm with a Synergy HT Multi-Mode Microplate Reader (Biotek).

Cell migration assays are typically performed in transwell membrane filter inserts in 24-well tissue culture plates (BD Biosciences). The transwell membrane filter inserts can be, for example, 6.5-mm diameter, 8-μm pore size, and 10-nm thick polycarbonate membranes.

Invasion assays are performed in BD Biocoat Growth Factor Reduced Matrigel Invasion Chambers (BD Biosciences). The cancer cell lines are harvested and resuspended in CM from osteocytes with or without the test reagent. Cancer cell suspensions are added to the upper side of the inserts. Cells are incubated at 37° C. for various periods of time. Cells that do not migrate through the filters are removed, and cells that migrate through the inserts are fixed and stained with Hema 3 Stat Pack (Fisher Scientific). The number of migrated cells in 5 fields of view per insert is counted under a light microscope.

In certain aspects breast cancer migration is decreased when incubated in CM from osteocytes treated with AD or FFSS to stimulate Cx43 hemichannel opening. When osteocyte Cx43 hemichannels were blocked by E2 antibody, this inhibitory effect on cancer cell migration was attenuated. This decrease in cancer cell migration is not seen when incubated with CM collected from osteoblasts or when treated directly with AD. Opening of Cx43 hemichannels is protective against breast cancer cell growth and migration.

B. In Vivo Assays

Other embodiments are directed to detection of connexin hemichannel opening in vivo. One example of an in vivo assay for discovery of reagents useful in treating cancer metastasis to bone includes determining the effect of a candidate reagent on Cx43 hemichannels in osteocytes and on cancer bone metastasis in vivo. In certain aspects Cx43 modulation in osteocytes is determined by injecting candidate reagents into a long bone and using fluorescence tracer dyes (e.g., calcein or Evans blue) to detect the opening of hemichannels in osteocytes in situ.

Determining the Effect a Compound on the Opening of Hemichannels in Osteocytes in Bone Tissue In Vivo.

One example of an in vivo assay to analyze hemichannels in osteocytes uses 3-4 month old mice or rats. The animals are weighed. A test reagent is introduced into the animal through intraperitoneal (IP) injection. After 2-4 hours, fluorescence tracer dyes (i.e. Evans blue, Alexa 594) are injected into lateral tail vein of the animal or by IP injection. Note: up to 1% of animal's body weight in volume can be injected. In certain aspects the animal is warmed prior to tail vein injection to dilate the tail vein. After 2-4 hours, the animal is scarified and tibial and femur bones free of muscle tissues are dissected and washed multiple times with PBS. The bone is fixed in paraformaldehyde and decalcified in 14% EDTA solution at 4° C. for two weeks or room temperature under constant agitation for 3-5 days. The bone is washed in PBS and soaked in 30% sucrose in PBS overnight and embedded in OCT compound. Position of the bone is typically adjusted in the mold as needed. Five μm thick frozen sections are cut using a cryostat, the sections rinsed in PBS, and mounted using 50% glycerol in PBS. The bone sections can be examined under fluorescence microscope and the degree of osteocytes in the bone taking up tracer dyes are quantified using Image J.

The opening of Cx43 hemichannels in osteocytes can be confirmed by mechanical loading on tibias opening Cx43 hemichannels in osteocytes. This can serve as a positive control for hemichannel opening in osteocytes in vivo. For negative control, mice with the deficiency of Cx43 in osteocytes are used. This mouse is generated by crossing with 10-kb DMP-1 Cre and Cx43 flox mice.

The effect of the testing reagent on bone metastasis in vivo is determined using an intratibial injection bone metastasis model and/or intracardiac injection cancer metastasis assay.

Intratibial Injection Bone Metastasis Model.

The methods include anesthesizing 1-month old, normal or immunocompromised mice using isoflurane. The mice are also given buprenorphine-HCl (0.3 mg/ml) as an analgesic. Intratibial injections are performed using cancer cells expressing fluorescence or chemiluminescence markers (e.g., Py8119 cells expressing Luc-GFP to normal mice or Luc-GFP-expressing MD-MBA-231 to immunocompromised mice). The cancer cells are inoculated into the bone marrow area of right tibias through a pre-made hole made by a Hamilton syringe fitted with a 30-gauge needle. PBS was injected into the left tibias as control. The testing reagent or saline is administered IP twice a week for 5 weeks. Intratibial tumor growth is monitored with bioluminescence imaging or fluorescence every week starting from 3 days after tumor cell inoculation. At the termination of the study after sufficient bioluminescence imaging, X-ray images are taken to test bone quality and labeled metastatic cancer cell colonies are observed and counted with a fluorescence microscope.

Intracardiac Injection Bone Metastasis Model.

Two-three month old, normal or immunocompromised mice are anesthetized by isoflurane and are also given buprenorphine-HCl (0.3 mg/ml) as an analgesic. Cancer cells expressing fluorescence or chemiluminescence markers (e.g., Py8119 cells expressing Luc-GFP to normal mice or Luc-GFP-MD-MBA-231 to immunocompromised mice) are injected into the left cardiac ventricle of mice. The procedure includes: Holding the needle angled towards the operator and to the right, insert it into the second intercostal space, approximately 3 mm to the left of the sternum. Advance about 5 mm and turn the needle gently until the pulsatile flow of bright red arterial blood is observed entering the hub. Inject the cell suspension over 30 sec. Withdraw the needle and apply pressure on the injection site for 30 sec using an alcohol wipe. Place the mouse on a warmed surface until it has fully recovered from anesthesia. Perform bioluminescent or fluorescent imaging after intracardiac injection to verify distribution of tumor cells every week from 3 days after tumor cell inoculation. At the termination of the study after sufficient bioluminescence imaging, X-ray images are taken to assess bone quality and labeled metastatic cancer cell colonies are observed and counted with a fluorescence microscope.

Cx43 Conditional Knock Out (cKO) Mice.

Because homozygous Cx43 global knockouts are lethal, and also because the inventors want to examine the role of Cx43 expressed in osteocytes, osteocyte-specific Cx43 knockout mice were generated. Crossing mice homozygous for the floxed Cx43 gene with Cx43 global heterozygous mice to facilitate the complete deletion of Cx43 in osteocytes. Cx43fl/− mice (50% of progeny) were then crossed with mice expressing Cre recombinase driven by the human DMP-1 promoter. This created mice that were Cx43 fl/−, DMP 1 Cre+ or Cx43 fl/−, DMP 1 Cre− (small percentage are Cx43fl/fl or Cx43−/−). Cx43 deficient osteocytes were confirmed by immunohistochemistry.

Studies can include 4 groups of mice: WT treated with alendronate (AD), KO treated with alendronate, WT without AD, and KO without alendronate. AD was administered to the mice at 150 µg/kg body weight. With AD treatment it is expected bone metastasis will increase in KO compared to WT mice. And without AD treatment bone metastasis should be similar between WT and knockout mice.

II. Methods of Treating Conditions Associated with Connexin Hemichannels

In certain embodiments modulators of connexin hemichannels can be used to treat disorders associated with connexin hemichannels, including inflammatory disorders such as osteoarthritis (OA) and spinal injury. The methods and compositions described herein can also be used to treat wounds such as corneal and skin wounds.

A. Osteoarthritis (OA)

Osteoarthritis is a prevalent disease that affects proximate 20% of adults in the United States. This disease causes the degeneration of joints including articular cartilage and subchondral bone. The pathology of OA is characterized by a loss of articular cartilage leading to narrowing of joint space, increased joint friction and potential structure remodeling. The current treatment includes exercise, lifestyle change and analgesics. If symptoms become severe, joint replacement surgery is normally performed. Thus far, there is no specific pharmaceutical intervention available for the treatment of OA.

Chondrocytes express connexin (Cx) 43 hemichannels, and these channels mediate the passage of small molecules (less than 1 kDa) between inside/outside of the cell. Under normal condition, Cx43 hemichannels in chondrocytes remain closed; however, these channels are open under inflammatory conditions and release small molecules such as pro-inflammatory factors. The mechanical loading and interleukin-β1 induce the opening of Cx43 hemichannels in chondrocytes promote inflammatory response with the release of inflammatory promoting factors such as prostaglandin E2 (PGE2) and ATP.

Inhibiting the opening of Cx43 hemichannels in chondrocytes (e.g., by chemical reagents, etc.), can suppress the inflammation and the development of osteoarthritis. The hemichannel opening in chondrocytes can be detected using the methods described herein. The release of pro-inflammatory factors (PGE2 and ATP) by Cx43 hemichannels is measured using ELISA assays. Agents that block the opening of hemichannels can be used a therapeutic for inflammatory disorders such as OA.

Elevated interleukin 1β (IL-1β) is an inducer of OA. Abnormal joint loading is also known to increase the risk of OA. The exposure of IL-1β causes the release of prostaglandins and NO by chondrocytes. The released $PGE_2$ exerts catabolic effects by inhibiting proteoglycan synthesis and inducing collage degradation. It has been shown that mechanical loading opens Cx43 hemichannels. Cx43 serves as a portal for the $PGE_2$ release in bone cells. Cx43 is expressed on the surface of chondrocytes (see FIG. 18) and in articular cartilage. IL-1β and mechanical loading caused the opening of Cx43 hemichannels in chondrocytes (FIG. 18) and this opening was inhibited by hemichannel-specific Cx43 antibody. When hemichannels are blocked by Cx43 (E2) antibody, the inflammatory response evoked by IL-1β was inhibited.

Based on above evidence, Cx43 hemichannels in chondrocytes are open by IL-1β or mechanical loading, and $PGE_2$ released by hemichannels leading to the development of OA. Specific blockade of Cx43 hemichannels in chondrocytes may be used in a therapeutic strategy for the treatment of OA caused by elevated IL-1β or trauma (abnormal loading).

In vitro cell models for evaluating Cx43 channel activity. Primary chondrocytes are isolated from joints of mouse leg bones. An agent's effect on Cx43 hemichannel opening and gap junction coupling in chondrocytes can be detected and the time and dosage-dependent effects evaluated. For example, hemichannel opening is assessed by dye uptake assay, using Lucifer yellow or Alexa dyes. Downstream effects are measured by detecting release of $PGE_2$ and ATP using ELISA assays.

With spinal injuries, local inflammation and swelling often result from localized injury, trauma, or infection and the same events can also be the cause of systemic inflammation. Inflammation is often characterized by increased redness, swelling, temperature, pain, and some loss of function in the affected area. In certain aspects agents that inhibit hemichannels opening can be used to ameliorate inflammation associated with central nervous system inflammation and/or spinal cord injury.

Wound healing represents another significant health issue and entails a complex biological process regardless of causation. In general, the wound is cleaned by infiltrating cells and fluids during the associated inflammatory response. This initial inflammatory phase is followed by a proliferative phase where different cell types provide the necessary factors and tissue environment for wound healing or filling-in by appropriate cells such as fibroblasts, keratinocytes, and a variety of others. Additional events such as angiogenesis and contraction of the wound as epithelial cells gradually fill-in the wound also occur. This phase tends to last about 7-10 days depending upon the severity of the wound and the efficiency of the inflammatory phase. Circumstances such as older age, immunodeficiency, as well as stress, and other environmental factors can affect wound healing. Extended exposure of the wound leads to increased possibilities of infection, adverse inflammatory effects, as well as scarring and possibly chronic wounds. Generally, the wound healing process resolves with the maturation and remodeling phase. Collagen is replaced, remodeled, and cross-linked, thereby increasing the strength of the newly developed tissue and unnecessary blood vessels, cells and tissues are slowly removed from the wound site. This final phase can last up to several years as the body tends to the final healing stage.

Treatments for wounds typically involve the application of antibiotics as well as agents that provide protection from the external environment such as bandages, stitches, second skin, sealants, or other creams and salves. Additionally, numerous compounds are also available for treatment of inflammation in the early phase of wound healing, often in combination with steroidal anti-inflammatory compounds or pharmaceuticals. Agents described herein or identified by the methods described herein can be used to modulate the inflammatory processes associated with wound healing.

III. Antibodies

Certain aspects of the invention are directed to antibodies that modulate, positively or negatively, the function of hemichannels. An example of identifying and isolating a monoclonal antibody is described below.

The term "CDR" as used herein refers to a Complementarity Determining Region of an antibody variable domain. Systematic identification of residues included in the CDRs have been developed by Kabat et al. (1991, Sequences of Proteins of Immunological Interest, 5th Ed., United States Public Health Service, National Institutes of Health, Bethesda). Variable light chain (VL) CDRs are herein defined to include residues at positions 27-32 (CDR1), 50-56 (CDR2), and 91-97 (CDR3). Variable heavy chain (VH) CDRs are herein defined to include residues at positions 27-33 (CDR1), 52-56 (CDR2), and 95-102 (CDR3).

As will be appreciated by those in the art, the CDRs disclosed herein may also include variants. Generally, the amino acid identity between individual variant CDRs is at least 90%, 91%, 92%, 93%, 94%, 95%, 96%, 97%, 98%, 99%, or 100%. Thus, a "variant CDR" is one with the specified identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities as described herein.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein, or any other antibody embodiments as outlined herein.

By "Fv" or "Fv fragment" or "Fv region" as used herein is meant a polypeptide that comprises the VL and VH domains of a single antibody.

By "framework" as used herein is meant the region of an antibody variable domain exclusive of those regions defined as CDRs. Each antibody variable domain framework can be further subdivided into the contiguous regions separated by the CDRs (FR1, FR2, FR3 and FR4).

The term "antigen-binding portion" of an antibody (or simply "antibody portion"), as used herein, refers to one or more fragments of an antibody that retain the ability to specifically bind to an antigen (e.g., hemichannel). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VLNK, VH, CL and CH1 domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3rd ed. 1993); (iv) a Fd fragment consisting of the VH and CH1 domains; (v) a Fv fragment consisting of the VL and VH domains of a single arm of an antibody; (vi) a dAb fragment (Ward et al., (1989) Nature 341:544-546), which consists of a VH domain; (vii) an isolated complementarity determining region (CDR); and (viii) a nanobody, a heavy chain variable region containing a single variable domain and two constant domains.

The term "specifically binds" (or "immunospecifically binds") is not intended to indicate that an antibody binds exclusively to its intended target. Rather, an antibody "specifically binds" if its affinity for its intended target is about 5-fold greater when compared to its affinity for a non-target molecule. Suitably there is no significant cross-reaction or cross-binding with undesired substances. The affinity of the antibody will, for example, be at least about 5 fold, such as 10 fold, such as 25-fold, especially 50-fold, and particularly 100-fold or more, greater for a target molecule than its affinity for a non-target molecule. In some embodiments, specific binding between an antibody or other binding agent and an antigen means a binding affinity of at least $10^6$ M$^{-1}$. Antibodies may, for example, bind with affinities of at least about $10^7$ M$^{-1}$, such as between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{11}$ M$^{-1}$. Antibodies may, for example, bind with an EC$_{50}$ of 50 nM or less, 10 nM or less, 1 nM or less, 100 pM or less, or more preferably 10 pM or less.

Mouse mAb Purification Protocol.

Protein G rather than Protein A is the column of choice for purifying mouse IgGs, because mouse IgG1 binds much better to Protein G. Supernatants from Hybridoma cultures without fetal calf serum were collected after 15 days, in order to produce IgG.

In an experiment a GammaBind Plus™ Sepharose Fast flow column was used. The column was cleaned and then equilibrated with binding buffer. About 30 ml of buffer solution was used for each of these steps. Diluted hybridoma supernatant whit binding buffer was then loaded on the column. Fractions of 1.5 ml (elution) were collected. 150 µl of 1 M Tris buffer with pH 8 was used to neutralize the pH. The column was re-equilibrated with binding buffer (30-50 ml). Finally 20 µl of sodium azide was added for storage. The column binding capacity is 18 mg/ml of mouse IgG. 1 ml/min flow rate was used. 50 mM Na phosphate buffer saline with pH 7 was used as binding buffer and 0.1 M glycine with pH 2.7 was used as elution buffer. The supernant is mixed 1:1 ratio with the binding buffer.

In certain embodiments a mouse monoclonal antibody (M1) was used to study functions of connexin Cx43 forming gap junctions or/and hemichannels, where the heavy chain of monoclonal antibody has as amino acid sequence set forth in SEQ ID NO:2 and the light chain of the of monoclonal antibody M1 has an amino acid sequence set forth in SEQ ID NO:4.

In certain embodiments a mouse monoclonal antibody (M2) was used to study functions of connexin Cx43 forming gap junctions or/and hemichannels, where the heavy chain of monoclonal antibody has an amino acid sequence set forth in SEQ ID NO:6 and the light chain of the of monoclonal antibody has an amino acid sequence set forth in SEQ ID NO:8.

In certain embodiments a mouse monoclonal antibody (M7) was used to study functions of connexin Cx43 forming gap junctions or/and hemichannels, where the heavy chain of monoclonal antibody has an amino acid sequence set forth in SEQ ID NO: 10 and the light chain of the of monoclonal antibody has an amino acid sequence set forth in SEQ ID NO: 12.

Immunoblots.

MLO-Y4 Cells were seeded $3\times10^5$ at 60 mm dishes for 48 h. Mouse heart tissues were collected in lysis buffer (5 mM Tris, 5 mM EDTA, 5 mM EGTA plus protease inhibitors, 20 l/4 ml phenylmethylsulfonyl fluoride (PMSF), 20 µl/ml N-ethylmaleimide, 10 µl/ml $NaVO_4$ and 10 µl/ml leupeptin), homogenized and centrifuged at 100,000×g at 4° C. for 30 min and resuspended in lysis buffer. Crude membrane proteins were separated by 10% SDS-polyacrylamide gel electrophoresis, transferred to nitrocellulose membranes and blotted with anti-Cx43 CT (1:300 dilution) recognizing the C-terminus of Cx43 or anti-Cx43 E2 (1:500 dilution) recognizing the second extracellular loop of Cx43 or the monoclonal antibodies against the second extracellular loop of Cx43 (1:100 dilution). Secondary antibodies, infrared IRDye® 800 anti-rabbit IgG (1:15000) (LI-COR, Lincoln, Nebr., USA), fluorescence was detected with Odyssey infrared detection system (LI-COR, Lincoln, Nebr., USA).

Immunofluorescence.

MLO-Y4 cells were cultured on collagen-coated glass coverslip. The cells were rinsed 2 times with PBS and incubated with cold 70% ethanol for 20 min at −20° C. The use of PFA destroys the epitope, which is lysine rich, therefore not recommended. Then the cells were rinsed twice with PBS in order to remove the ethanol. After that the cells were blocked with blocking solution (2% goat serum, 2% fish skin gelatin, and 1% bovine serum albumin in PBS) overnight. Then, the cells were labeled with monoclonal antibodies at different concentrations in PBS, followed by FITC-conjugated goat anti-mouse antibody and WGA-alexa594 (Invitrogen) (1:400 and 1:1500 in blocking solution respectively). The cells were observed by Olympus BH-2 fluorescence microscopy and the images were processed offline with NIH Image J software.

Dye Uptake for Hemichannel Activities.

Dye uptake measurements were evaluated using snap shot photographs. MLO-Y4 cells were plated on the collagen coated 35 mm dish and incubated with recording medium, $HCO_3^-$ free saline medium buffered with 10 mM HEPES salt composition in mM, 154 NaCl, 5.4 KCl, 1.8 $CaCl_2$, 1.0 $MgCl_2$, 5 Glucose. Medium with low concentration of divalent cation (low[$X^2$]) was added 0.5 mM EGTA but not $CaCl_2$ and $MgCl_2$. The recording or low[$X^2$] containing 50 µM EtBr for snap shot recording. Cells were exposed to 100 µM of EtBr during 5 min, then rinsed 3 times with PBS and fixed with 2% formamide. At least 3 microphotographs of fluorescence fields were taken with a 10× dry objective in an inverted microscope (Carl Zeiss) with a rhodamine filter. The image analysis was made offline with the software image J. The average of pixel density of 30 random cells was measured.

Dye Coupling Assay for Gap Junctions.

MLO-Y4 cells were plated on collagen coated 35 mm dish and incubated with recording medium ($HCO_3^-$ free αMEM medium buffered with 10 mM HEPES). Cells were microinjected using a micromanipulator InjectMan NI 2 and Femtojet both from Eppendorf (Eppendorf) at 37° C. with alexafluor 350 (Invitrogen, Eugene, Oreg., USA) (10 mM in PBS). Dye transfer was measured after 2 minutes of alexafluor 350 injection. The index of dye coupling was scored counting the number of cells that were dye transferred. Dye coupling was observed under an inverted microscope equipped with Xenon arc lamp illumination and a Nikon eclipse (Nikon, Japan) (excitation wavelengths 330-380 nm; emission wavelengths above 420 nm).

Cell Parachute Dye-Transfer Assay for Gap Junctions.

MLO-Y4 cells were grown to confluence in 12 well plates. The donor cells were incubated with 5 µM calcein red-orange-AM (790 Da) and 5 µM Oregon green 488 BAPTA-2-AM (1752 Da) for 40 minutes at 37° C. Gap junction intercellular communication can be followed by simultaneously labeling cells with calcein red-orange as a gap junction permeable tracer dye and the gap junction channel impermeable dye Oregon green 488 BAPTA-2. Donor cells preloaded were remove form the plate by trypsinization. Preloaded cells were layered ('parachuted') over the top of the unlabeled recipient cells cultured in at a 1:4 donor to receiver ratio. Cells were allowed to attach for various periods 1 hours, and then carefully washed 3 times and fixed in fresh 2% PFA 10 min RT and rinse 3 times again. The cells were examined with a fluorescence microscope. For calcein red-orange transfer, the threshold was adjusted to clearly distinguish the dye-transfer boundaries. The dye transfer positive criterion was detecting the calcein red-orange/Oregon green 488 BAPTA-2 with contact cells calcein red-orange positive and Oregon green 488 BAPTA-2 negative. The dye transfer was almost undetectable (<1%). The images were taken in places where we found Oregon green 488 BAPTA-2 green positive cells.

Fluid Flow Shear Stress to Open Hemichannels.

Fluid flow was created by parallel-plate flow chambers separated by a gasket of defined thickness with gravity-driven fluid flow using a peristaltic pump. The thickness of the gasket determined the channel height, which was adjusted along with flow rate to generate stress levels of 16 dyn/cm². The circulating medium was α-MEM buffered with 10 mM HEPES.

The examples provided as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

IV. Pharmaceutical Compositions

Certain aspects include a composition, e.g., a pharmaceutical composition, containing one or a combination of monoclonal antibodies, or antigen-binding portion(s) thereof formulated with a pharmaceutically acceptable carrier. Such compositions may include one or a combination of (e.g., two or more different) antibodies, or immunoconjugates described herein. For example, a pharmaceutical composition of the invention can comprise a combination of antibodies that bind to different epitopes on the target antigen or that have complementary activities.

Pharmaceutical compositions of the invention also can be administered as combination therapy, i.e., combined with other agents. For example, the combination therapy can include an anti-hemichannel antibody combined with at least one other anti-cancer agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, or parenteral administration (e.g., by injection or infusion). Depending on the route of administration, the active compound, i.e., antibody, or immunoconjugate, may be coated in a material to protect the compound from the action of acids and other natural conditions that may inactivate the compound.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-hemichannel antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-hemichannel antibody results in a decrease in severity of disease symptoms, an increase in frequency and duration of disease symptom-free periods, or a prevention of impairment or disability due to the disease affliction. A therapeutically effective amount of a therapeutic compound or antibody can decrease tumor metastasis, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, or other parenteral routes of administration, for example by injection or infusion. The phrase "parenteral administration" as used herein means modes of administration other than enteral and topical administration, usually by injection, and includes, without limitation, intravenous, intramuscular, intraarterial, intraperitoneal, transtracheal, subcutaneous, subcuticular, intraarticular injection and infusion.

The invention claimed is:

1. An antibody or antigen-binding portion thereof, comprising: a first, second and third heavy chain complementarity determining region (CDR) sequence from the heavy chain sequence of SEQ ID NO: 2, wherein the first, second and third heavy chain CDR sequences are located at amino acid positions 27-33, 52-56 and 95-102, numbered according to the Kabat numbering system, of the heavy chain amino acid sequence of SEQ ID NO: 2, respectively; and a first, second and third light chain CDR sequence from the light chain sequence of SEQ ID NO: 4, wherein the first, second and third light chain CDR sequences are located at amino acid positions 27-32, 50-56 and 91-97, numbered according to the Kabat numbering system, of the light chain amino acid sequence of SEQ ID NO: 4, respectively.

2. The antibody of claim 1, wherein the heavy chain amino acid sequence is at least 90% identical to the amino acid sequence of SEQ ID NO: 2, and the light chain amino acid sequence is at least 90% identical to the amino acid sequence of SEQ ID NO: 4.

3. The antibody of claim 2, wherein the antibody inhibits the opening of a Cx43 hemichannel.

4. The antibody of claim 1, wherein antibody binds to a Cx43 hemichannel.

5. The antibody of claim 1, wherein the heavy chain variable domain comprises the amino acid sequence of SEQ ID NO: 2; and the light chain variable domain comprises the amino acid sequence of SEQ ID NO: 4.

6. A pharmaceutical composition comprising the antibody or antigen-binding fragment thereof of claim 1 and a pharmaceutically acceptable carrier.

7. The pharmaceutical composition of claim 6, wherein the antibody is a monoclonal antibody.

8. The pharmaceutical composition of claim 6, wherein the pharmaceutical composition is lyophilized.

9. A method of inhibiting the opening of a Cx43 hemichannel, the method comprising contacting a population of cells, wherein in at least some of the cells express Cx43 hemichannels in the brain or spinal cord, with an effective amount of a composition comprising an antibody or antigen-binding fragment thereof, wherein the antibody or antigen-binding fragment thereof, comprises:
  a first, second and third heavy chain CDR sequence from the heavy chain sequence of SEQ ID NO: 2, wherein the first, second and third heavy chain CDR sequences are located at amino acid positions 27-33, 52-56 and 95-102, numbered according to the Kabat numbering system, of the heavy chain amino acid sequence of SEQ ID NO: 2, respectively; and a first, second and third light chain CDR sequence from the light chain sequence of SEQ ID NO: 4, wherein the first, second and third light chain CDR sequences are located at amino acid positions 27-32, 50-56 and 91-97, numbered according to the Kabat numbering system, of the light chain amino acid sequence of SEQ ID NO: 4, respectively; wherein the antibody or antigen-binding fragment thereof binds to a Cx43 hemichannel.

10. The method of claim 9, wherein the heavy chain of the antibody or antigen-binding fragment thereof comprises a heavy chain variable domain comprising an amino acid sequence that is at least 90% identical to the amino acid sequence of SEQ ID NO: 2; and a light chain variable domain comprising an amino acid sequence that is at least 90% identical to the amino acid sequence of SEQ ID NO: 4.

11. The method of claim 9, wherein the antibody or antigen-binding fragment thereof binds to a Cx43 eptiope having an amino acid sequence selected from SEQ ID NO: 13, SEQ ID NO: 14, or SEQ ID NO: 15.

12. The method of claim 9, wherein the antibody is a single chain antibody.

13. The method of claim 9, wherein the antibody or antigen-binding fragment thereof is linked to a detectable label.

14. The method of claim 9, wherein the antigen-binding fragment is a Fab fragment, an Fab' fragment or an F(ab')2 fragment.

15. The method of claim 9, wherein the composition further comprises an adjuvant, a protein, a peptide, a fluorescent dye.

16. A method of inhibiting the opening of a Cx43 hemichannel in a subject, the method comprising administering to the subject an effective amount of an antibody or antigen-binding portion thereof, wherein the antibody or antigen-binding portion thereof, comprises:
  first, second and third heavy chain CDR sequence from the heavy chain sequence of SEQ ID NO: 2, wherein the first, second and third heavy chain CDR sequences are located at amino acid positions 27-33, 52-56 and 95-102, numbered according to the Kabat numbering system, of the heavy chain amino acid sequence of SEQ ID NO: 2, respectively; and a first, second and third light chain CDR sequence from the light chain sequence of SEQ ID NO: 4, wherein the first, second and third light chain CDR sequences are located at amino acid positions 27-32, 50-56 and 91-97, numbered according to the Kabat numbering system, of the light chain amino acid sequence of SEQ ID NO: 4, respectively; and/or
  wherein the antibody or antigen-binding portion thereof binds to a Cx43 hemichannel.

17. The method of claim 16, wherein the antibody or antigen-binding portion thereof, comprises: a) a heavy chain variable domain comprising an amino acid sequence that is at least 90% identical to the amino acid sequence of SEQ ID NO: 2; and b) a light chain variable domain comprising an amino acid sequence that is at least 90% identical to the amino acid sequence of SEQ ID NO: 4.

18. The method of claim 16, wherein the antibody is a monovalent antibody.

19. The method of claim 16, wherein the antibody is a bivalent antibody.

20. The method of claim 16, wherein the antibody is a monoclonal antibody.

21. The method of claim 16, wherein the antibody or antigen-binding portion thereof binds to a Cx43 eptiope having an amino acid sequence selected from SEQ ID NO: 13, SEQ ID NO: 14, or SEQ ID NO: 15.

* * * * *

SEQUENCE LISTING

```
<160> NUMBER OF SEQ ID NOS: 15

<210> SEQ ID NO 1
<211> LENGTH: 384
<212> TYPE: DNA
<213> ORGANISM: Mus musculus

<400> SEQUENCE: 1
gaggttcagc tggagcagcc tggggctgaa ctggtgaagc ctggggcttc agtgaagttg      60
tcctgcaagg cttctggcta caccttcacc agctactata tgtactgggt gaagcagagg     120
cctggacaag gccttgagtg gattggggga attaatccta gcaatggtgg tactaacttc     180
aatgagaagt tcaagaacaa ggccacactg actgtagaca atcctccag cacagcctac      240 atgcaactca gcagcctgac atctgaggac tctgcggtct attactgtac aagagagggt     300 aaccectact atactatgaa ctactggggt caaggaacct cagtcaccgt ctcctcagcc     360
aaaacgacac ccccatctgt ctat                                            384

<210> SEQ ID NO 2
<211> LENGTH: 128
<212> TYPE: PRT
<213> ORGANISM: Mus musculus

<400> SEQUENCE: 2

Glu Val Gln Leu Glu Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Lys Ala Thr Leu Thr Val Asp Lys Ser Ser Ser Thr Ala Tyr
```

```
                65                  70                  75                  80
Met Gln Leu Ser Ser Leu Thr Ser Glu Asp Ser Ala Val Tyr Tyr Cys
                        85                  90                  95

Thr Arg Glu Gly Asn Pro Tyr Tyr Thr Met Asn Tyr Trp Gly Gln Gly
            100                 105                 110

Thr Ser Val Thr Val Ser Ser Ala Lys Thr Thr Pro Pro Ser Val Tyr
        115                 120                 125

<210> SEQ ID NO 3
<211> LENGTH: 324
<212> TYPE: DNA
<213> ORGANISM: Mus musculus

<400> SEQUENCE: 3
gatattgtga tgacacagac tcctgcttcc ttagctgtat ctctggggca gagggccacc      60
atctcataca gggccagcaa aagtgtcagt acatctggct atagttatat gcactggaac     120
caacagaaac caggacagcc acccagactc ctcatctatc ttgtatccaa cctagaatct     180
ggggtccctg ccaggttcag tggcagtggg tctgggacag acttcaccct caacatccat     240
cctgtggagg aggaggatgc tgcaacctat tactgtcagc acattaggga gcttacacgt     300
tcggaggggg gaccaagctg gaaa                                            324

<210> SEQ ID NO 4
<211> LENGTH: 108
<212> TYPE: PRT
<213> ORGANISM: Mus musculus

<400> SEQUENCE: 4

Asp Ile Val Met Thr Gln Thr Pro Ala Ser Leu Ala Val Ser Leu Gly
 1               5                  10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Gly Gly Pro Ser Trp Lys
            100                 105

<210> SEQ ID NO 5
<211> LENGTH: 384
<212> TYPE: DNA
<213> ORGANISM: Mus musculus

<400> SEQUENCE: 5
gaggttcagc tggagcagcc tggggctgaa ctggtgaagc ctggggcttc agtgaagttg      60
tcctgcaagg cttctggcta caccttcacc agctactata tgtactgggt gaagcagagg     120
cctggacaag gccttgagtg gattggggga attaatccta gcaatggtgg tactaacttc     180
aatgagaagt tcaagaacaa ggccacactg actgtagaca atcctccag cacagcctac      240 atgcaactca gcagcctgac atctgaggac tctgcggtct attactgtac aagagagggt     300 aaccccctact atactatgaa ctactgggt caaggaacct cagtcaccgt ctcctcagcc     360
```
aaaacgacac ccccatctgt ctat                                          384

<210> SEQ ID NO 6
<211> LENGTH: 128
<212> TYPE: PRT
<213> ORGANISM: Mus musculus

<400> SEQUENCE: 6

Glu Val Gln Leu Glu Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Glu Gly Asn Pro Tyr Tyr Thr Met Asn Tyr Trp Gly Gln Gly
            100                 105                 110

Thr Ser Val Thr Val Ser Ser Ala Lys Thr Thr Pro Pro Ser Val Tyr
        115                 120                 125

<210> SEQ ID NO 7
<211> LENGTH: 375
<212> TYPE: DNA
<213> ORGANISM: Mus musculus

<400> SEQUENCE: 7
gatattgtga tgacccagac tccatcctcc ctgagtgtgt cagcaggaga gaaggtcact      60
atgagctgca agtccagtca gagtctgtta acagtggaa atcaaaagac ctacttggcc     120
tggtaccagc agaaaccagg gcagcctcct aaactgttga tctacggggc atccactagg     180
gaatctgggg tccctgatcg cttcacaggc agtggatctg gaaccgattt cactcttacc     240
atcagcagtg tgcaggctga agacctggca gtttattact gtcagaatga tcatagttat     300
ccattcacgt tcggctcggg gacaaagttg gaaataaaac gggctgatgc tgcaccaact     360
gtatccgcat gcacc                                                     375

<210> SEQ ID NO 8
<211> LENGTH: 122
<212> TYPE: PRT
<213> ORGANISM: Mus musculus

<400> SEQUENCE: 8

Asp Ile Val Met Thr Gln Thr Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Thr Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
            85                  90                  95

Asp His Ser Tyr Pro Phe Thr Phe Gly Ser Gly Thr Lys Leu Glu Ile
            100                 105                 110

Lys Arg Ala Asp Ala Ala Pro Thr Val Ser
            115                 120

<210> SEQ ID NO 9
<211> LENGTH: 405
<212> TYPE: DNA
<213> ORGANISM: Mus musculus

<400> SEQUENCE: 9
ctggagcagc ctggggctga actggtgagg cctggggctt cagtaatgct gtcctgcaag      60
gcttctggct acatcttcac cacctactgg atgcactggc tgaagcagag gcctggacaa     120
ggccttgact ggattggaga gattagtcct agcaacggtc gttctaatta caataagaag     180
ttcaagagca aggccacact gactgtagac aaatcctcca gcacagccta catgcaactc     240
agcagcctga catctgagga ctctgcggtc tattactgtg cacgattcga cgagggggac     300
ttctggggcc aaggcaccac tctcatagtc tcctcagcca aaacaacagc cccatcggtc     360
tatccactgg cccctgtgtg tggagataca actggctcct cggtg                    405

<210> SEQ ID NO 10
<211> LENGTH: 135
<212> TYPE: PRT
<213> ORGANISM: Mus musculus

<400> SEQUENCE: 10

Leu Glu Gln Pro Gly Ala Glu Leu Val Arg Pro Gly Ala Ser Val Met
1               5                   10                  15

Leu Ser Cys Lys Ala Ser Gly Tyr Ile Phe Thr Thr Tyr Trp Met His
            20                  25                  30

Trp Leu Lys Gln Arg Pro Gly Gln Gly Leu Asp Trp Ile Gly Glu Ile
        35                  40                  45

Ser Pro Ser Asn Gly Arg Ser Asn Tyr Asn Lys Lys Phe Lys Ser Lys
    50                  55                  60

Ala Thr Leu Thr Val Asp Lys Ser Ser Ser Thr Ala Tyr Met Gln Leu
65                  70                  75                  80

Ser Ser Leu Thr Ser Glu Asp Ser Ala Val Tyr Tyr Cys Ala Arg Phe
            85                  90                  95

Asp Glu Gly Asp Phe Trp Gly Gln Gly Thr Thr Leu Ile Val Ser Ser
            100                 105                 110

Ala Lys Thr Thr Ala Pro Ser Val Tyr Pro Leu Ala Pro Val Cys Gly
            115                 120                 125

Asp Thr Thr Gly Ser Ser Val
            130             135

<210> SEQ ID NO 11
<211> LENGTH: 324
<212> TYPE: DNA
<213> ORGANISM: Mus musculus

<400> SEQUENCE: 11
gatattgtga tgacacagac tcctgcttcc ttagctgtat ctctggggca gagggccacc      60
atctcataca gggccagcaa aagtgtcagt acatctggct atagttatat gcactggaac     120

```
caacagaaac caggacagcc acccagactc ctcatctatc ttgtatccaa cctagaatct    180
ggggtccctg ccaggttcag tggcagtggg tctgggacag acttcaccct caacatccat    240
cctgtggagg aggaggatgc tgcaacctat tactgtcagc acattaggga gcttacacgt    300
tcggaggggg gaccaagctg gaaa                                          324
```

```
<210> SEQ ID NO 12
<211> LENGTH: 108
<212> TYPE: PRT
<213> ORGANISM: Mus musculus

<400> SEQUENCE: 12
```

Asp Ile Val Met Thr Gln Thr Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105

```
<210> SEQ ID NO 13
<211> LENGTH: 10
<212> TYPE: PRT
<213> ORGANISM: Artificial Sequence
<220> FEATURE:
<223> OTHER INFORMATION: synthetic peptide

<400> SEQUENCE: 13
```

Phe Leu Ser Arg Pro Thr Glu Lys Thr Ile
1               5                   10

```
<210> SEQ ID NO 14
<211> LENGTH: 10
<212> TYPE: PRT
<213> ORGANISM: Artificial Sequence
<220> FEATURE:
<223> OTHER INFORMATION: synthetic peptide

<400> SEQUENCE: 14
```

Lys Arg Asp Pro Cys Pro His Gln Val Asp
1               5                   10

```
<210> SEQ ID NO 15
<211> LENGTH: 9
<212> TYPE: PRT
<213> ORGANISM: Artificial Sequence
<220> FEATURE:
<223> OTHER INFORMATION: synthetic peptide

<400> SEQUENCE: 15
```

Leu Ser Ala Val Tyr Thr Cys Lys Arg
1               5